United States Patent (10) Patent No.: US 10,010,879 B2
Sawamura et al. (45) Date of Patent: Jul. 3, 2018

(54) PHOSPHINE TRIPLY CROSS-LINKED BY ORGANIC POLYMER, TRANSITION METAL COMPLEX USING SAID PHOSPHINE AS A LIGAND, AND CATALYST

(71) Applicants: National University Corporation Hokkaido University, Sapporo-shi, Hokkaido (JP); Tosoh Organic Chemical Co., Ltd., Yamaguchi (JP)

(72) Inventors: Masaya Sawamura, Sapporo (JP); Tomohiro Iwai, Sapporo (JP); Tomoya Harada, Sapporo (JP)

(73) Assignee: Tosoh Organic Chemical Co., Ltd, Shunan, Yamaguchi (JP)

(*) Notice: Subject to any disclaimer, the term of this patent is extended or adjusted under 35 U.S.C. 154(b) by 217 days.

(21) Appl. No.: 14/772,424

(22) PCT Filed: Mar. 6, 2014

(86) PCT No.: PCT/JP2014/055860
§ 371 (c)(1),
(2) Date: Jan. 4, 2016

(87) PCT Pub. No.: WO2014/136909
PCT Pub. Date: Sep. 12, 2014

(65) Prior Publication Data
US 2016/0136628 A1 May 19, 2016

(30) Foreign Application Priority Data

Mar. 7, 2013 (JP) ................. 2013-045650

(51) Int. Cl.
| | |
|---|---|
| C08F 212/14 | (2006.01) |
| B01J 31/24 | (2006.01) |
| C08F 8/42 | (2006.01) |
| C07C 1/32 | (2006.01) |
| B01J 31/16 | (2006.01) |
| C08F 12/14 | (2006.01) |
| C08F 212/08 | (2006.01) |
| C08F 212/12 | (2006.01) |
| C08F 230/02 | (2006.01) |

(52) U.S. Cl.
CPC ....... *B01J 31/2404* (2013.01); *B01J 31/1658* (2013.01); *C07C 1/321* (2013.01); *C08F 8/42* (2013.01); *C08F 12/14* (2013.01); *C08F 212/08* (2013.01); *C08F 212/12* (2013.01); *C08F 212/14* (2013.01); *B01J 2231/4227* (2013.01); *B01J 2231/4277* (2013.01); *B01J 2231/4283* (2013.01); *B01J 2531/16* (2013.01); *B01J 2531/821* (2013.01); *B01J 2531/822* (2013.01); *B01J 2531/824* (2013.01); *B01J 2531/827* (2013.01); *B01J 2531/828* (2013.01); *B01J 2531/847* (2013.01); *C07C 2531/24* (2013.01); *C08F 230/02* (2013.01)

(58) Field of Classification Search
CPC ......... C08F 212/08; C08F 8/42; C08F 230/02
See application file for complete search history.

(56) References Cited

FOREIGN PATENT DOCUMENTS

| | | |
|---|---|---|
| JP | H0249009 A | 2/1990 |
| JP | 2007302859 A | 11/2007 |

OTHER PUBLICATIONS

Leadbeater et al. Chem. Rev. 2002, 102, 3217-3274.*
Supporting infromation for Lloret et al. Organometallics 2008, 27, 850-856.*
International Search Report (with English translation) and Written Opinion dated Apr. 28, 2014 in International Application No. PCT/JP2014/055860.
International Preliminary Report on Patentability dated Feb. 10, 2015 in International Application No. PCT/JP2014/055860.
Lloret et al., "ortho-Metalated Dirhodium(II) Catalysts Immobilized on a Polymeric Cross-Linked Support by Copolymerization. Study of their Catalytic Activity in the Asymmetric Cyclopropanation of Styrene with Ethyl Diazoacetate," Organometallics, vol. 27, pp. 850-856 (2008).

(Continued)

*Primary Examiner* — Mark S Kaucher
(74) *Attorney, Agent, or Firm* — Panitch Schwarze Belisario & Nadel LLP

(57) ABSTRACT

Provided are: a polymer-supported phosphane compound exhibiting excellent catalytic reaction activity; a complex including the compound and a transition metal; and a catalyst including the complex. This polymer compound includes: units of threefold styrene cross-linked phosphane; and styrene units having substituent groups (R) in position 4 (provided that R represents hydrogen, a C1-6 lower alkyl group, a C1-6 lower alkoxy group, or a polar functional group). In the formula in which the polymer compound includes structure (1), PS represents a polystyrene unit chain including the styrene units having the substituent groups (R). The complex includes the polymer and a transition metal. The catalyst for an organic compound coupling reaction includes the complex.

(1)

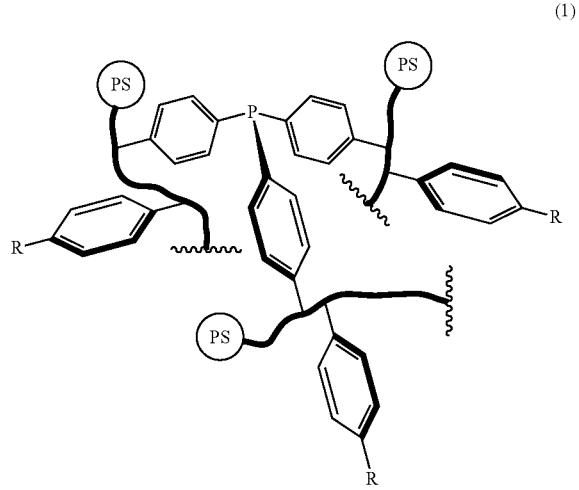

23 Claims, No Drawings

(56) References Cited

OTHER PUBLICATIONS

Kawamorita et al., "Rh-Catalyzed Borylation of N-Adjacent C(sp3)-H Bonds with a Silica-Supported Triarylphosphine Ligand," Journal of the American Chemical Society, vol. 134, pp. 12924-12927 (2012).

Miyazaki et al., "Rh-Catalyzed Direct Borylation of sp3 C—H Adjacent to N Atom with Silica-Supported Cage-Type Triarylphosphine," CSJ: The Chemical Society of Japan Koen Yokoshu, vol. 92, No. 4, p. 1431 (2012).

Harada et al., "Synthesis of Polystyrene-cross-linking Tripod Phosphines and Application to Transition Metal Catalyzed C—H and C—Cl Transformation Reactions," CSJ: The Chemical Society of Japan Koen Yokoshu, vol. 93, No. 4, p. 1534 (2013).

Harada et al., "Development of threefold cross-linked polystyrene triarylphosphane and application to inactive bond transformation reaction," 112nd CATSJ Meeting, p. 440 (2013).

Iwai et al., "Threefold Cross-Linked Polystyrene-Triphenylphosphane Hybrids: Mono-P-Ligating Behavior and Catalytic Applications for Aryl Chloride Cross-Coupling and C(sp3)-H Borylation," Angewandte Chemie International Edition, vol. 52, pp. 12322-12326 (2013).

Grubbs et al., "Catalytic Reduction of Olefins with a Polymer-Supported Rhodium(I) Catalyst," Journal of the American Chemical Society, vol. 93, No. 12, pp. 3062-3063 (Jun. 16, 1971).

McKenzie et al., "Polymer-Supported Phosphines: Reactivity of Pendant and Crosslink Groups," Journal of Polymer Science, vol. 20, pp. 431-441 (1982).

\* cited by examiner

PHOSPHINE TRIPLY CROSS-LINKED BY ORGANIC POLYMER, TRANSITION METAL COMPLEX USING SAID PHOSPHINE AS A LIGAND, AND CATALYST

CROSS-REFERENCE TO RELATED APPLICATION

This application is a Section 371 of International Application No. PCT/JP2014/055860, filed Mar. 6, 2013, which was published in the Japanese language on Sep. 12, 2014, under International Publication No. WO 2014/136909 A1, and the disclosure of which is incorporated herein by reference.

CROSS-REFERENCE TO RELATED APPLICATIONS

This application claims benefit of priority to Japanese Patent Application No. 2013-45650 filed on Mar. 7, 2013, which is expressly incorporated herein by reference in its entirety.

BACKGROUND ART

Polymer-supported phosphane-transition metal catalyst, which is easily separable by filtration from a reaction mixture and is therefore recyclable, is advantageous in view of reducing environmental impact in material production, and is expected to be put into industrial use. A supported phosphane, prepared by a conventional method of preparing a polymer-supported phosphane, that is, a copolymerization method of using a ligand unit having a single polymerizable point, a monomer, and a cross-linking agent, has been known that it often shows a catalytic activity equivalent to or lower than that of a correspondent homogeneous catalyst, due to difficulties in controlling the steric hindrance of the active center and the support, and the coordination environment (Non-Patent Literature 1).

As for cross-linked polymer manufactured by using, as a cross-linking agent, a phosphane derivative having a plurality of polymerizable points, two reports below have been known. A first report has been made on a polystyrene-supported phosphane using bis(4-vinylphenyl)phenylphosphane as a cross-linking agent (Non-Patent Literature 2).

A second reports has been made on a polystyrene-supported phosphane-rhodium complex, obtained by using, as a threefold cross-linker, a complex configured by a dirhodium (II) complex coordinated with two tris(4-vinylphenyl)phosphane units (Non-Patent Literature 3).

[Non-Patent Literature 1] Grubbs, J. Am. Chem. Soc. 1971, 93, 3062.
[Non-Patent Literature 2] Sherrington, J. Ploym. Sci. Pol. Chem. Ed. 1982, 20, 431.
[Non-Patent] Úbeda, Organometallics 2008, 27, 850.

SUMMARY OF INVENTION

The polymer-supported phosphane described in Non-Patent Literature 2 is a twofold cross-linked, polymer-supported triarylphosphane, wherein the polymer is not used as a ligand of a metal complex catalyst. The present inventors prepared a metal complex using this twofold cross-linking phosphane as a ligand, and experimentally applied it to a coupling reaction, only to find that it was unlike a metal complex catalyst of our invention capable of showing a high catalytic activity.

Non-Patent Literature 3 describes a metal complex using a threefold cross-linked polymer-supported triarylphosphane. According to the method described in Non-Patent Literature 3, the starting material is, however, restricted to the preliminarily prepared dirhodium(II) complex, and the product shows only a catalytic activity lower than that of the correspondent homogenous rhodium complex. Also, there is no description on replacement of the dirhodium(II) complex with other metal species, after the cross-linking agent was used for the polymerization reaction.

It is therefore an object of this invention to provide a polymer-supported phosphane compound showing a high catalytic reaction activity, a complex composed of such compound and a transition metal, and a catalyst containing such complex.

The present inventors used, as a cross-linking agent, a ligand unit having a plurality of polymerizable points introduced therein, and allowed it to copolymerize with a variety of monomers to produce novel threefold cross-linked polymer-supported phosphane compounds, and found that, by using these cross-linked polymer-supported phosphane compounds as the ligands, it now became possible to freely manufacture phosphane-metal (1:1) complexes with a wide variety of transition metal species. The findings led the present inventors to work out this invention.

Note that the dirhodium(II) complex described in Non-Patent Literature 3, having two phosphane moieties positioned close to each other, is explicitly different from the copolymer of this invention capable of spatially isolating the phosphanes. Moreover, the dirhodium(II) complex described in Non-Patent Literature 3 cannot reserve a reaction space around the metal coordination point, and is also in this point explicitly different from the compound of this invention. The metal complex described in Non-Patent Literature 3 is prepared by polymerizing the preliminarily-prepared dirhodium(II) complex. However, as for a polymer having the phosphane moiety but no rhodium, neither a method of preparation nor a polymer per se is described in Non-Patent Literature 3.

This invention includes the followings:

[1]
A polymer compound comprising a threefold styrene cross-linked phosphane unit and styrene units each having a substituent R on the 4-position, wherein R represents a hydrogen atom, lower alkyl group having 1 to 6 carbon atoms, lower alkoxy group having 1 to 6 carbon atoms or polar functional group, and wherein the compound may comprise two or more varieties of styrene units having different (R)s.

[2]
The polymer compound described in [1], comprising a structure (1) below:

[Chemical Formula 1]

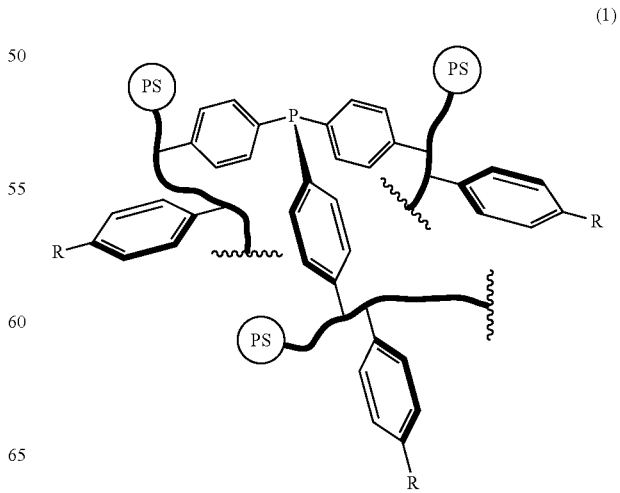

(1)

in the formula, PS represents a polystyrene unit chain composed of styrene units each having a substituent R.

[3]
The polymer compound described in [1], wherein the compound is a copolymer of a tris(4-vinylphenyl)phosphane unit and styrene units each having a substituent R, wherein the styrene units each having a substituent R are styrene units having the same substituent (R)s, or two or more varieties of styrene units having different substituent (R)s, and the two or more varieties of styrene units having different substituent (R)s are contained in the polymer compound with random arrangement.

[4]
The polymer compound described in [3], wherein the equivalence ratio of the tris(4-vinylphenyl)phosphane unit and the styrene units each having a substituent R falls in the range of 1:(20 to 1000).

[5]
The polymer compound described in [3] or [4], wherein the copolymer further contains cross-linkage through a divinylbenzene unit.

[6]
The polymer compound described in [5], wherein the equivalence ratio of the tris(4-vinylphenyl)phosphane unit, the styrene units each having a substituent R and the divinylbenzene unit falls in the range of 1:(20 to 1000):(0.1 to 20).

[7]
The polymer compound described in any one of [1] to [6], wherein the compound exhibiting a swelling volume in toluene or cyclopentyl methyl ether of 2.0 to 7.0 mL/g.

[8]
The polymer compound described in any one of [1] to [7], wherein the polar functional group is a hydroxy group, polyether group, acetoxy group, ester group or amide group.

[9]
The polymer compound described in any one of [1] to [8], wherein the polymer compound contains no metal.

[10]
A complex comprising the polymer compound described in any one of [1] to [8], and a transition metal.

[11]
The complex described in [10], further comprising, as a ligand, halogen, carbonyl, hydroxy, nitro, amino, sulfonyl, or cyano.

[12]
The complex described in [10], wherein the carbonyl is assignable to ester, aldehyde, ketone or amide.

[13]
The complex described in any one of [10] to [12], wherein the transition metal is palladium, iridium, rhodium, platinum, ruthenium, nickel, or copper.

[14]
A catalyst for a coupling reaction of organic compound, comprising the complex described in any one of [10] to [13].

[15]
The catalyst for a coupling reaction of organic compound described in [14], wherein the coupling reaction of organic compound is C—C coupling reaction, C—N coupling reaction or $C(sp^3)$-H borylation.

In the polymer compound of this invention, each phosphane which offers a metal coordination point is located at a network node where three polymer chains (polystyrene unit chains) are bundled. Such nodes are accessible to each other only with difficulty in the polymer chain, instead the individual phosphanes are supposed to be spatially isolated. Accordingly, in the complex of the polymer compound and transition metal of this invention, the transition metal and phosphane are supposed to selectively form a 1:1 complex.

In addition, also the straight chain moieties of the polymer chains are less accessible to such network nodes (threefold cross-linkage point), and this consequently reserves a space around the node. In short, the catalytic active center which is located at the node is kept in a sufficiently large reaction field, without being affected by steric hindrance of the polymer chains.

Synergistically owing to these two effects, a transition metal complex, configured using the polymer compound of this invention containing the threefold cross-linked phosphane as the ligand, supposedly made it possible to provide a highly active catalytic reaction field. Note, however, that the present inventors have no intention of adhering to the theory described above, and the fact remains that the transition metal complex of this invention shows a high activity as a consequence.

In fact, as illustrated by EXAMPLE, by using the copolymer of this invention, which is a cross-linked polystyrene manufactured by using tris(4-vinylphenyl)phosphane as a cross-linker, a cross-coupling reaction of aryl chlorides with the aid of a palladium catalyst will proceed in an efficient manner.

This invention is also effective to a catalytic reaction which involves cleavage of a less reactive aliphatic carbon-hydrogen bond, such as borylation of a secondary $C(sp^3)$-H bond of 2-alkyl pyridine assisted by an iridium catalyst, and borylation of a $C(sp^3)$-H bond next to a nitrogen atom assisted by a rhodium catalyst.

According to this invention, by manufacturing the threefold cross-linked phosphane-containing polymer compound, and then adding a variety of metal complexes, it now becomes possible to freely create highly-controlled, heterogeneous transition metal complex catalysts. The catalysts are applicable to a variety of coupling reactions.

DESCRIPTION OF EMBODIMENTS

<Threefold Cross-Linked Phosphane-Containing Polymer Compound>

This invention relates to a threefold cross-linked phosphane-containing polymer compound. The polymer compound contains a threefold styrene cross-linked phosphane unit, and styrene units each having a substituent R on the 4-position. R possessed by the styrene unit having a substituent R is a hydrogen atom, lower alkyl group having 1 to 6 carbon atoms, lower alkoxy group having 1 to 6 carbon atoms or polar functional group. The polymer compound of this invention is specifically a polymer compound which contains the structure (1) below:

[Chemical Formula 2]

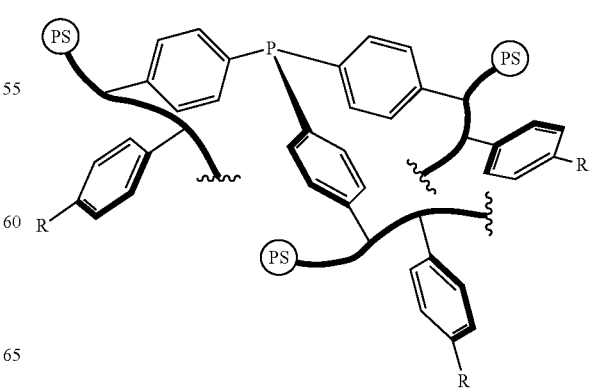

(1)

In formula (1), PS represents a polystyrene unit chain composed of the styrene units each having the substituent R. The substituent R was described above.

More specifically, the polymer compound of this invention may be a copolymer of tris(4-vinylphenyl)phosphane unit, which corresponds to the threefold styrene cross-linked phosphane unit, and styrene units each having the substituent R. The copolymer may be a random copolymer which randomly contains the tris(4-vinylphenyl)phosphane unit, and a copolymerizable component composed of the styrene units each having the substituent R. The tris(4-vinylphenyl) phosphane unit is a unit configured by tris(4-vinylphenyl) phosphane (compound 1) shown below which is incorporated into the polymer while bound through vinyl groups. In this specification, the styrene unit having the substituent R may occasionally be referred to simply as styrene unit.

[Chemical Formula 3]

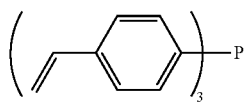

1

The copolymerizable component is incorporated into the polystyrene unit chain, by using the above-described tris(4-vinylphenyl)phosphane as the copolymerization monomer. Since the tris(4-vinylphenyl)phosphane is trifunctional, so that all of the individual vinyl groups may be incorporated into different polystyrene unit chains, to thereby obtain a copolymer configured so that a single tris(4-vinylphenyl) phosphane as a copolymerization unit is contained in three polystyrene unit chains. In this way, the threefold styrene cross-linked phosphane unit is formed. Note, however, that also obtainable is a copolymer configured so that a single tris(4-vinylphenyl)phosphane as a copolymerization unit is contained in a single or two polystyrene unit chains, so that the copolymer of this invention also encompasses a mixture of a copolymer in which a single tris(4-vinylphenyl)phosphane is contained as the copolymerization unit in three polystyrene unit chains, and a copolymer in which the copolymerization unit is contained in one or two polystyrene unit chains. While the polystyrene unit chains PS in the copolymerizable component are illustrated independently in formula (1), the individual polystyrene unit chains may also be independent in the portions not illustrated, or may alternatively be coupled with other polystyrene unit chain PS illustrated in the formula.

While the amount of introduction of the tris(4-vinylphenyl)phosphane unit in the copolymer of this invention is not specifically limited, the content in terms of equivalence ratio of the styrene unit, assuming the content of the tris(4-vinylphenyl)phosphane unit as unity, may be 10 to 1000. Note, however, that for the case where the copolymer of this invention is used as a ligand for a metal complex described later, the content of the tris(4-vinylphenyl)phosphane unit is preferably set to a relatively high value, from the viewpoint of obtaining a high catalytic activity per unit amount, since phosphorus of the tris(4-vinylphenyl)phosphane unit serves as a coordination site on a metal, and a resultant metal complex is used as a catalyst. An excessive amount of the tris(4-vinylphenyl)phosphane unit, however, makes the tris(4-vinylphenyl)phosphane units too close to each other, thereby the copolymerization reaction may be slowed down due to steric hindrance, and the obtained copolymer may have an increased ratio of cross-linkage to degrade the handleability. Taking these aspects into consideration, assuming now the amount of the tris(4-vinylphenyl)phosphane unit as unity, the amount of styrene unit falls in the range from 20 to 200 in equivalence ratio, preferably from 30 to 150, and even more preferably from 40 to 100. Note that a preferable range of the equivalence ratio also varies depending on the species of R.

When R represents a hydrogen atom, the polystyrene unit chain PS in the copolymer of this invention other than the copolymerization unit of tris(4-vinylphenyl)phosphane is composed of a styrene unit. When R represents a group other than hydrogen atom, each styrene unit of the polystyrene unit chain PS has the R as a substituent. Alternatively, each of the styrene units of the polystyrene unit chains PS may have, as R, at least two species selected from hydrogen atom, lower alkyl group having 1 to 6 carbon atoms, lower alkoxy group having 1 to 6 carbon atoms and polar functional group. The different (R)s in this case may be arranged randomly. The tris(4-vinylphenyl)phosphane unit may be introduced into the polystyrene unit chain PS again randomly. The copolymer of this invention is, therefore, a random copolymer.

The copolymer of this invention, when intended to be used as a catalyst in the form of complex with a transition metal, may also be improved in the catalytic activity, by introducing a residue other than hydrogen atom as the substituent R on the aromatic ring of the styrene unit. The lower alkyl group having 1 to 6 carbon atoms which exemplifies R may be methyl group, ethyl group, n-propyl group, i-propyl group, n-butyl group, i-butyl group, t-butyl group, n-pentyl group or n-hexyl group; and the lower alkoxy group having 1 to 6 carbon atoms may be methoxy group, ethoxy group, n-propoxy group, i-propoxy group, n-butoxy group, or t-butoxy group. The polar functional group is exemplified by hydroxyl group, polyether group, acetoxy group, ester group, and amide group. The polyether group is exemplified by oligomer or polymer chain having ethylene glycol units, where the number of ethylene glycol units is typically 2 or larger, and 100 or smaller. The polyether group is more specifically exemplified by tetraethylene glycol monomethyl ether group. The ester group is exemplified by those formed with a lower alkyl group having 1 to 6 carbon atoms, and is specifically exemplified by methyl ester group, and ethyl ester group. Substituent of the acyl group in the amide group is exemplified by lower alkyl group having 1 to 6 carbon atoms, and more specifically by methyl amide group, and ethyl amide group. The substituent R capable of largely improving the catalytic activity is exemplified by methyl group and t-butyl group.

The plurality of polystyrene unit chains in the copolymer of this invention may contain cross-linkage using a divinylbenzene unit. By introducing the cross-linkage composed of divinylbenzene unit into the copolymer of this invention, the copolymer may be controlled in strength, and also improved in moldability. Note, however, that since also the tris(4-vinylphenyl)phosphane unit has a function of cross-linking the polystyrene unit chains, so that introduction of only the tris(4-vinylphenyl)phosphane unit, without introducing the cross-linkage by divinylbenzene unit, will be sufficient for controlling the strength and for improving the moldability of the copolymer. The amount of introduction of the divinylbenzene unit may be suitably determined, taking the amount of introduction of tris(4-vinylphenyl)phosphane unit, and desired levels of strength and moldability of the copolymer into consideration.

The amount cross-linkage by the divinylbenzene unit may be suitably determined taking the ratio of contents of the styrene unit and the tris(4-vinylphenyl)phosphane unit into consideration. For an exemplary case where 60 equivalent of styrene unit is allowed to copolymerize with one equivalent of tris(4-vinylphenyl)phosphane unit as described in EXAMPLE, and further the divinylbenzene unit is allowed to copolymerize therewith, the equivalence ratio of the divinylbenzene unit is suitably selectable in the range, for example, from 0.1 to 5, and also in the range from 0.2 to 4. As the amount of introduction of the divinylbenzene unit increases as described above, the copolymer may be enhanced in strength, or may be improved in moldability.

When the copolymer contains the divinylbenzene unit, it is more typical to control the equivalence ratio of the tris(4-vinylphenyl)phosphane unit, the styrene unit and the divinylbenzene unit in the range of 1:(20 to 1000):(0.1 to 20) for example. More preferable range is 1:(30 to 200):(0.1 to 10), even more preferable range is 1:(35 to 200):(0.1 to 10), and yet more preferable range is 1:(40 to 200):(0.1 to 10). Divinylbenzene may be m-divinylbenzene, p-divinylbenzene, or mixture of them. Divinylbenzene may occasionally contain ethyl vinyl benzene as an impurity for manufacture reasons, and also such divinylbenzene containing the impurity may be used. In this case, the obtainable copolymer of this invention may contain not only the divinylbenzene unit, but also an ethyl vinyl benzene unit.

It is technically difficult to determine the molecular weight of the polymer compound (copolymer) of this invention, since it is a cross-linked polymer compound (copolymer). In place of molecular weight or degree of polymerization, swelling volume in an organic solvent will be denoted. The polymer compound (copolymer) of this invention shows the swelling volume in the range from 2.0 to 7.0 mL/g in any of organic solvents including hexane, dichloromethane, toluene, t-butyl methyl ether, tetrahydrofuran, cyclopentyl methyl ether, diethyl ether, acetone, ethyl acetate, dimethylformamide, and methanol. The swelling volume preferably falls in the range from 3.0 to 6.0 mL/g. It is particularly preferable that the swelling volume in toluene or cyclopentyl methyl ether falls in the range from 2.0 to 7.0 mL/g, and more preferably from 3.0 to 6.0 mL/g.

The copolymer of this invention may be synthesized by random copolymerization of tris(4-vinylphenyl)phosphane and styrene having substituent R; or by random copolymerization of tris(4-vinylphenyl)phosphane, the styrene having substituent R and divinylbenzene. Tris(4-vinylphenyl)phosphane (Compound 1 in EXAMPLE) is reported in *Organometallics* 2008, 27, 850. The literature, however, gives no description on detailed method of synthesis and spectral data. An exemplary synthesis of this compound, as Compound 1, will be described later in EXAMPLE. Styrene containing R and divinylbenzene are commercially available. The substituent R of styrene containing substituent R is same as those previously described about the styrene unit having substituent R, wherein R is a hydrogen atom, lower alkyl group having 1 to 6 carbon atoms, lower alkoxy group having 1 to 6 carbon atoms or polar functional group. By using at least two varieties of styrenes having different substituents R, it also becomes possible to obtain a copolymer which contains styrene units having two varieties of substituents R.

The copolymer may be synthesized typically by suspension polymerization of a predetermined ratio of such two or three varieties of monomers, using a known polymerization initiator. The suspension polymerization may be implemented typically at 50 to 100° C. for 1 to 72 hours. These ranges are, however, not intended to be limitative, and may be suitably determined depending on species and ratio of monomers used as the source materials, species and amount of polymerization initiator to be used, and conditions of the suspension polymerization.

<Complex>

The complex of this invention includes the polymer compound (copolymer) of this invention and a transition metal. The transition metal is exemplified by the first series transition elements (3d transition elements), the second series transition elements (4d transition elements) and the third series transition elements (5d transition elements). The first series transition elements are exemplified by scandium (Sc), titanium (Ti), vanadium (V), chromium (Cr), manganese (Mn), iron (Fe), cobalt (Co), nickel (Ni), copper (Cu), and zinc (Zn). The second series transition elements are exemplified by yttrium (Y), zirconium (Zr), niobium (Nb), molybdenum (Mo), technetium (Tc), ruthenium (Ru), rhodium (Rh), palladium (Pd), silver (Ag), and cadmium (Cd). The third series transition elements (5d transition elements) are exemplified by tungsten (VV), rhenium (Re), osmium (Os), iridium (Ir), platinum (Pt), gold (Au), and lead (Pb). From the viewpoint of catalytic activity, the transition metal is preferably palladium (Pd), iridium (Ir), rhodium (Rh), platinum (Pt), ruthenium (Ru), nickel (Ni), copper (Cu) and so forth. These elements are, however, not intended to be imitative. The complex of this invention contains, as a ligand, the copolymer of this invention. Phosphorus (P) of the tris(4-vinylphenyl)phosphane unit in the copolymer of this invention coordinates to the transition metal.

The complex of this invention may further contain a functional group such as halogen (fluorine, chlorine, bromine, iodine), carbonyl (ester, aldehyde, ketone, amide), hydroxy, nitro, amino, sulfonyl or cyano, which have been commonly used as a ligand of transition metal complex. Varieties and the number (the number of coordination on a single transition metal) of these ligands are suitably determined depending on the species of transition metal. The complex of this invention may be prepared by mixing a transition metal and the above-described polymer compound (copolymer) of this invention having one or two or more species of ligands, in an organic solvent. The organic solvent used here is suitably selectable, for example, from toluene used in EXAMPLE, and organic solvents for use in measurement of the swelling volume of the polymer compound (copolymer) of this invention.

In the complex of this invention, the equivalence ratio of the tris(4-vinylphenyl)phosphane unit in the polymer compound (copolymer) of this invention and the transition metal is 1:1. In other words, one metal and one tris(4-vinylphenyl) phosphane unit are bound to form the complex. The complex of this invention is configured so that the metal complex is formed in at least a part of the tris(4-vinylphenyl)phosphane unit in the polymer compound (copolymer). The larger the content of the tris(4-vinylphenyl)phosphane unit in the polymer compound (copolymer) which forms the metal complex, the better, from the viewpoint that the complex of this invention is intended to be used as a catalyst, as described later, with a high catalytic activity per unit mass. For example, 50 to 100%, preferably 70 to 100%, and more preferably 90 to 100% of the tris(4-vinylphenyl)phosphane unit in the copolymer forms the metal complex.

<Catalyst>

This invention also relates to a catalyst for coupling reaction, which contains the complex of this invention. The coupling reaction refers to a reaction of producing a new bond between carbon in an organic compound and carbon in an organic compound, or between carbon in an organic compound and a heteroatom in an organic compound. The coupling reaction is exemplified by C—C coupling reaction, C—N coupling reaction, and C(sp$^3$)-H borylation.

Suzuki-Miyaura coupling is a representative coupling, which is preferably a reaction of allowing an aryl halide or alkenyl halide to condense with an aryl boron derivative or alkenyl boron derivative, to thereby produce a diaryl derivative, alkenylaryl derivative or 1,3-dienes. A specific example may be a method of condensing, for example, a benzene halide and a phenylboronic acid to produce biphenyl.

Halogen in the organic halide is exemplified by chlorine atom, bromine atom, and iodine atom. Aryl group in the aryl halide is exemplified by carbocyclic aromatic group and heterocyclic aromatic group. The carbocyclic aromatic group is exemplified by monocyclic, polycyclic or condensed-ring carbocyclic aromatic groups having 6 to 36 carbon atoms, preferably 6 to 18 carbon atoms, or 6 to 12 carbon atoms. Such carbocyclic aromatic group is exemplified by phenyl group, naphthyl group, biphenyl group, phenanthryl group, and anthryl group. The heterocyclic aromatic group is exemplified by 3- to 8-membered, and preferably 5- to 8-membered monocyclic, polycyclic, and condensed-ring heterocyclic groups which contain 1 to 4, preferably 1 to 3, or 1 to 2 heteroatoms selected from nitrogen atom, oxygen atom and sulfur atom. Such heterocyclic group is exemplified by furyl group, thienyl group, pyrrolyl group, pyridyl group, indolyl group, and benzoimidazolyl group. These aryl groups may additionally have any of substituents selectable without limitation from those which will not adversely affect the reaction, which are exemplified by halogen atom, nitro group, substituted or unsubstituted alkyl group having 1 to 20, and preferably 1 to 10 carbon atoms, substituted or unsubstituted alkoxy group having 1 to 20, and preferably 1 to 10 carbon atoms, and substituted or unsubstituted alkoxy carbonyl group having 1 to 20, and preferably 1 to 10 carbon atoms. Alkenyl group in the alkenyl halide is a substituted or unsubstituted vinyl group, wherein substituent of the vinyl group is exemplified by substituted or unsubstituted alkyl group having 1 to 20, preferably 1 to 10 carbon atoms, substituted or unsubstituted alkenyl group having 1 to 20, preferably 1 to 10 carbon atoms, substituted or unsubstituted aryl group having 6 to 20, preferably 6 to 10 carbon atoms, and substituted or unsubstituted alkynyl group having 7 to 20, preferably 7 to 12 carbon atoms. Substituents for these are not specifically limited, so long as they will not adversely affect the reaction.

The boron derivative is exemplified by mono-, di- and tri-esters of orthoboric acid or derivatives thereof, but is not always limited to orthoboric acid or derivatives thereof. Aryl group of the aryl boron derivative is exemplified by aromatic rings such as substituted or unsubstituted phenyl group, naphthyl group, pyridyl group and furyl group, wherein the substituent thereof is selectable without special limitation from those which will not adversely affect the reaction, exemplified by halogen atoms such as chlorine atom, bromine atom or iodine atom; substituted or unsubstituted alkyl group having 1 to 20, preferably 1 to 10 carbon atoms; and substituted or unsubstituted alkoxy group having 1 to 20, preferably 1 to 10 carbon atoms. Alkenyl group of the alkenyl boron derivative is exemplified by substituted or unsubstituted vinyl group, where the substituent thereof is selectable without special limitation from those which will not adversely affect the reaction.

The coupling reaction is exemplified by Mizoroki-Heck reaction. This is a reaction for producing aryl alkenes or 1,3-diene, by a condensation reaction of alkenes with aryl halide or alkenyl halide.

The alkenes are exemplified by ethylene derivatives having at least one hydrogen atom. Exemplified preferably is ethylene derivatives in which at least one hydrogen atom of an ethylene is substituted by keto group, substituted or unsubstituted alkoxy carbonyl group, and/or, substituted or unsubstituted aryl group. The aryl group is exemplified by the above-described carbocyclic aromatic group and heterocyclic aromatic group. Substituents for these are not specifically limited so long as they will not adversely affect the reaction, and are exemplified by the above-described substituents. More preferable alkenes include substituted or unsubstituted 3-ketoalkenes, substituted or unsubstituted styrene derivatives, and substituted or unsubstituted (meth) acrylic esters. Ester residue of the acrylic esters is exemplified by substituted or unsubstituted alkyl group having 1 to 20, and preferably 1 to 10 carbon atoms, wherein the substituents thereof are not specifically limited so long as they will not adversely affect the reaction. Preferable examples of the alkenes are exemplified by, but not limited to, acrylic esters such as methyl acrylate, 3-ketoalkenes such as 3-ketobutene, and styrene derivatives including styrene.

Halogen in the organic halide is exemplified by chlorine atom, bromine atom and iodine atom. The aryl and alkenyl groups may be aliphatic and aromatic substituents, and are exemplified by substituted or unsubstituted vinyl group, and substituted or unsubstituted aryl group. The aryl group is exemplified by the above-described carbocyclic aromatic and heterocyclic aromatic group. Substituents for these are not specifically limited so long as they will not adversely affect the reaction.

The coupling reaction is also exemplified by Stille coupling. More specifically exemplified is a reaction of producing biaryls, aryl alkenes or 1,3-diene, by condensation reaction of aryl or alkenyl tin compound with aryl halide or alkenyl halide.

The substituent possessed by the tin compound is exemplified by aryl group, and more specifically by aromatic rings such as substituted or unsubstituted phenyl group, naphthyl group, pyridyl group, and furyl group. Substituents for these are not specifically limited so long as they will not adversely affect the reaction, and are exemplified by halogen atom such as chlorine atom, bromine atom or iodine atom; substituted or unsubstituted alkyl group having 1 to 20, preferably 1 to 10 carbon atoms; and substituted or unsubstituted alkoxy group having 1 to 20, preferably 1 to 10 carbon atoms. The tin compound may have an alkenyl group, wherein the alkenyl group is exemplified by substituted or unsubstituted vinyl group. Substituents for these are not specifically limited so long as they will not adversely affect the reaction.

The coupling reaction is also exemplified by Sonogashira coupling. More specifically exemplified is a reaction of producing aryl alkynes or alkenyl alkyne, by condensation reaction of alkynes with aryl halide or alkenyl halide.

Substituents of the alkynes are exemplified by aromatic groups such as substituted or unsubstituted phenyl group, naphthyl group, pyridyl group, and furyl group. Substituents for these are not specifically limited so long as they will not adversely affect the reaction, and are exemplified by halogen atoms such as chlorine atom, bromine atom and iodine atom; substituted or unsubstituted alkyl group having 1 to 20, preferably 1 to 10 carbon atoms, and substituted or unsubstituted alkoxy group having 1 to 20, preferably 1 to 10 carbon atoms. The substituents of the alkynes are also exemplified by substituted or unsubstituted vinyl group, wherein the substituents thereof are not specifically limited so long as they will not adversely affect the reaction.

Halogen in the organic halide is exemplified by chlorine atom, bromine atom and iodine atom. The aryl and alkenyl groups may be aliphatic and aromatic substituents, and are exemplified by substituted or unsubstituted vinyl group, and substituted or unsubstituted aryl group. The aryl group is exemplified by the above-described carbocyclic aromatic and heterocyclic aromatic group. Substituents for these are not specifically limited so long as they will not adversely affect the reaction.

The coupling reaction is also exemplified by Buchwald-Hartwig coupling. Specifically exemplified are reactions, through formation of carbon-oxygen bond or carbon-sulfur bond, and more preferably carbon-nitrogen bond, producing substituted amines, based on condensation reaction, for example, of amines having one or more alkyl groups or aryl groups with aryl halide or alkenyl halide.

Substituents of the amines are exemplified by substituted or unsubstituted alkyl group having 1 to 20, preferably 1 to 10 carbon atoms; and, aromatic groups such as substituted or unsubstituted phenyl group, naphthyl group, pyridyl group, and furyl group. Substituents for these are not specifically limited so long as they will not adversely affect the reaction, and are exemplified by halogen atoms such as chlorine atom, bromine atom and iodine atom; substituted or unsubstituted alkyl group having 1 to 20, preferably 1 to 10 carbon atoms; and substituted or unsubstituted alkoxy group having 1 to 20, preferably 1 to 10 carbon atoms.

Halogen in the organic halide is exemplified by chlorine atom, bromine atom and iodine atom. The aryl and alkenyl groups may be aliphatic and aromatic substituents, and are exemplified by substituted or unsubstituted vinyl group, and substituted or unsubstituted aryl group. The aryl group is exemplified by the above-described carbocyclic aromatic and heterocyclic aromatic group. Substituents for these are not specifically limited so long as they will not adversely affect the reaction.

The coupling reaction is also exemplified by C(sp$^3$)-H borylation. Specifically exemplified is a reaction of producing 2-(2-boron substituted alkyl)pyridines, based on condensation for example of 2-alkylpyridines with alkoxy boron derivative, through formation of carbon-boron bond.

Substituents of the pyridines are exemplified by substituted or unsubstituted alkyl group having 2 to 20, preferably 2 to 10 carbon atoms. Substituents for these are not specifically limited so long as they will not adversely affect the reaction, and are exemplified by aromatic groups such as phenyl group, naphthyl group, pyridyl group, and furyl group; halogen atoms such as chlorine atom, bromine atom and iodine atom; substituted or unsubstituted alkyl groups having 1 to 20, preferably 1 to 10 carbon atoms; and substituted or unsubstituted alkoxy group having 1 to 20, preferably 1 to 10 carbon atoms.

The alkoxy boron derivative is exemplified by substituted or unsubstituted alkoxy boron and alkoxy diboron having 1 to 20 carbon atoms, and derivatives thereof. Substituents thereof are not specifically limited so long as they will not adversely affect the reaction.

The coupling reaction is also exemplified by C(sp$^3$)-H borylation at the nitrogen-adjacent position. Specifically exemplified is a reaction of producing N-boron substituted alkylamides, based on condensation of N-alkylamides with alkoxy boron derivative, through formation of carbon-boron bond.

Substituents of the acyl group in the N-alkylamide group and N-alkylurea group is exemplified by substituted cyclic and acyclic alkyl groups having 1 to 20, preferably 2 to 10 carbon atoms. Additionally exemplified is substituted 2-aminopyridines having 1 to 20, preferably 2 to 10 carbon atoms. Substituents for these are not specifically limited so long as they will not adversely affect the reaction, and are exemplified by aromatic groups such as phenyl group, naphthyl group, pyridyl group, and furyl group; halogen atoms such as chlorine atom, bromine atom and iodine atom; substituted or unsubstituted alkyl group having 1 to 20, preferably 1 to 10 carbon atoms; and substituted or unsubstituted alkoxy group having 1 to 20, preferably 1 to 10 carbon atoms.

The alkoxy boron derivative is exemplified by substituted or unsubstituted alkoxy boron or alkoxy diboron having 1 to 20 carbon atoms, and derivatives thereof. Substituents for these are not specifically limited so long as they will not adversely affect the reaction.

In the coupling reaction using the catalyst of this invention, reaction conditions (solvent, temperature, time, etc.) are suitably determined depending on species of source materials and so forth. The reaction temperature is suitably selectable within the range from room temperature up to the boiling point of the solvent.

EXAMPLE

This invention will further be detailed referring to Examples. This invention is, however, not limited to Examples.

All synthetic operations were conducted using glass reactor vessels. The reactor vessels were used after heating, evacuation and cooling, and the reactions were allowed to proceed in an argon or nitrogen atmosphere. Reaction liquids were stirred using a Teflon (registered trademark)-coated magnetic stirrer bar. Reagents were purchased from Tokyo Chemical Industry Co., Ltd., Kanto Chemical Co., Inc., Wako Pure Chemical Industries, Ltd., and Sigma-Aldrich Corporation. Commercially available styrene and substituted styrene monomer were used after purified through an alumina column. Bis(pinacolato)diboron, purchased from AllyChem Co., Ltd., was used after removing a hexane-insoluble component by filtration at room temperature, and recrystallized from pentane. The solvents used here were dehydration grade products purchased from Kanto Chemical Co., Inc., and used after deaerated by a solidification-melting process, and further dehydrated over Molecular Sieve 4A.

NMR spectra (liquid) were measured using Varian Gemini 2000 ($^1$H; 300 MHz, $^{13}$C; 75.4 MHz, $^{31}$P; 121.4 MHz) NMR apparatus. Internal standards used here were tetramethylsilane ($^1$H) and deuterated chloroform ($^{13}$C), and external standard used here was an 85% phosphoric acid ($^{31}$P). CP/MAS NMR spectrum (solid) was measured using Bruker MSL-300 ($^{13}$C; 75.4 MHz, $^{31}$P; 121.4 MHz) NMR apparatus.

Synthesis of Tris(4-Vinylphenyl)Phosphane (Compound 1)

[Chemical Formula 4]

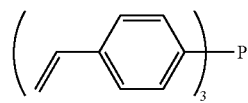

1

Compound 1 has been reported in *Organometallics* 2008, 27, 850. The literature, however, gives no description on detailed method of synthesis and spectral data.

In a 100 mL two-necked, eggplant-shaped flask, a stirrer and magnesium turnings (1.3 g, 54 mmol) were placed, then tetrahydrofuran (24 mL) and p-chlorostyrene (5.0 g, 36 mmol) were added sequentially under an argon atmosphere, the content was stirred for one hour while being refluxed under heating, to thereby prepare a correspondent organomagnesium reagent. Phosphorus trichloride (1.3 g, 10 mmol) was further added, and the mixture was stirred at room temperature for 6 hours. Water was added to the reaction liquid, the organic layer was extracted into chloroform, and then dried over dehydrated magnesium sulfate. The solvent was evaporated off under reduced pressure, followed by silica gel column chromatography (hexane:dichloromethane=4:1), to isolate Compound 1. Yield=2.0 g, percent yield=60%.

NMR data of Compound 1:
$^1$H NMR (CDCl$_3$): δ 5.28 (d, J=10.7 Hz, 3H), 5.78 (d, J=17.7 Hz, 3H), 6.71 (dd, J=17.7, 10.7 Hz 3H), 7.22-7.42 (m, 12H).
$^{13}$C NMR (CDCl$_3$): δ 114.77 (3C), 126.39 (d, J=7.4 Hz, 6C), 133.96 (d, J=19.4 Hz, 6C), 136.42 (3C), 136.69 (d, J=10.8 Hz, 3C), 138.06 (3C).
$^{31}$P NMR (CDCl$_3$): δ −6.3.

Synthesis of Phenylbis(4-Vinylphenyl)Phosphane (Compound 2)

[Chemical Formula 5]

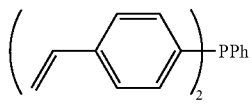

2

Compound 2 is a known compound (*J. Polym. Sci. Pol. Chem. Ed.* 1982, 20, 431).

In a 100 mL two-necked, eggplant-shaped flask, a stirrer and magnesium turnings (0.16 g, 6.6 mmol) were placed, then tetrahydrofuran (3 mL) and p-chlorostyrene (0.84 g, 6.0 mmol) were added sequentially under an argon atmosphere, the content was stirred for one hour while being refluxed under heating, to thereby prepare a correspondent organomagnesium reagent. A THF solution (20 mL) of phenyldichlorophosphane (0.36 g, 2.0 mmol) was then added, and the content was stirred at room temperature for 18 hours. Water was added to the reaction liquid, the organic layer was extracted into diethyl ether, and dried over dehydrated magnesium sulfate. The organic solvent was evaporated off under reduced pressure, followed by silica gel column chromatography (hexane:dichloromethane=4:1), to isolate Compound 2. Yield=0.44 g, percent yield=70%.

NMR Data of Compound 2:
$^1$H NMR (CDCl$_3$): δ 5.28 (d, J=11.2 Hz, 2H), 5.78 (d, J=17.7 Hz, 2H), 6.71 (dd, J=17.7, 11.2 Hz, 2H), 7.22-7.42 (m, 13H).
$^{13}$C NMR (CDCl$_3$): δ 114.69 (2C), 126.31 (d, J=6.9 Hz, 4C), 128.55 (d, J=6.9 Hz, 2C), 128.78, 133.70 (d, J=19.4 Hz, 2C) 133.93 (d, J=19.4 Hz, 4C), 136.36 (2C), 136.71 (d, J=10.8 Hz, 2C), 137.12 (d, J=10.8 Hz), 137.94 (2C). $^{31}$P NMR (CDCl$_3$): δ−5.8.

Synthesis of Diphenyl(4-Vinylphenyl)Phosphane (Compound 3)

[Chemical Formula 6]

3

Compound 3 is a known compound, and is also commercially available from Wako Pure Chemical Industries, Ltd. and Aldrich Corporation.

In a 100 mL two-necked, eggplant-shaped flask, a stirrer and magnesium turnings (0.16 g, 6.6 mmol) were placed, then tetrahydrofuran (3 mL) and p-chlorostyrene (0.84 g, 6.0 mmol) were added sequentially under an argon atmosphere, the content was stirred for one hour while being refluxed under heating, to thereby prepare a correspondent organomagnesium reagent. A THF solution (20 mL) of dichlorophenylphosphane (0.89 g, 4.0 mmol) was then added, and the content was stirred at room temperature for 18 hours. Water was added to the reaction liquid, the organic layer was extracted into diethyl ether, and dried over dehydrated magnesium sulfate. The organic solvent was evaporated off under reduced pressure, followed by silica gel column chromatography (hexane:dichloromethane=4:1), to isolate Compound 3. Yield=1.1 g, percent yield=97%.

NMR Data of Compound 3:
$^1$H NMR (CDCl$_3$): δ 5.28 (d, J=10.5 Hz, 1H), 5.78 (d, J=17.7 Hz, 1H), 6.71 (dd, J=17.7, 10.5 Hz, 1H), 7.21-7.42 (m, 14H).
$^{13}$C NMR (CDCl$_3$): δ 114.71, 126.34 (d, J=6.9 Hz, 2C), 128.58 (d, J=6.9 Hz, 4C), 128.81 (2C), 133.78 (d, J=19.5 Hz, 4C), 134.01 (d, J=19.5 Hz, 2C), 136.44, 136.64 (d, J=10.5 Hz), 137.19 (d, J=10.5 Hz, 2C), 137.99.
$^{31}$P NMR (CDCl$_3$): δ −5.4.

Synthesis of Threefold Cross-Linked Polystyrene-Phosphane 4

[Chemical Formula 7]

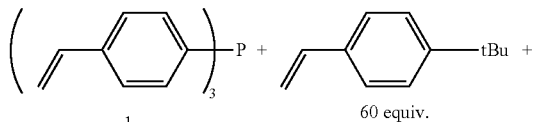

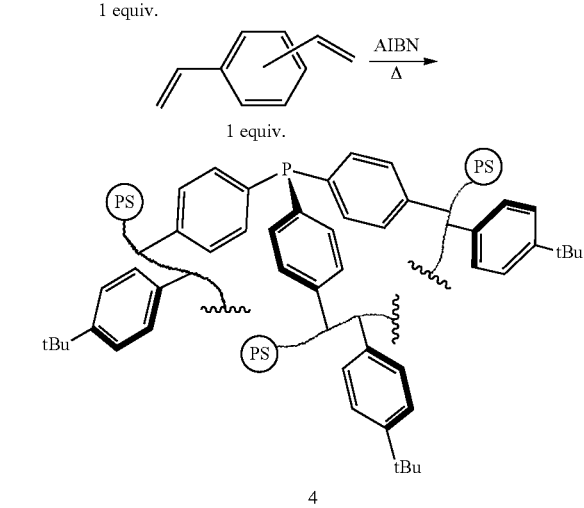

4

A stirrer bar was placed in a 500 mL eggplant-shaped flask, then under an argon atmosphere, Compound 1 (0.17 g, 0.50 mmol), p-(t-butyl)styrene (4.8 g, 30 mmol), divinylbenzene (0.13 g, purity >50% (containing ethylvinylbenzene), >0.50 mmol), water (120 mL) and chlorobenzene (6.0 mL) were sequentially added. To the mixture, sodium chloride (3.0 g), Arabic gum (4.8 g) and azobisisobutyronitrile (0.050 g, 0.30 mmol) were added, and the content was stirred under heating at 80° C. for 24 hours so as to allow suspension polymerization to proceed. The reaction mixture was cooled down to room temperature, the insoluble matter was collected by filtration, washed sequentially with water, methanol, toluene, THF, and methanol, and dried in vacuo at 80° C., to thereby obtain threefold cross-linked polystyrene-phosphane 4 in the form of white beady solid (4.6 g, 90 wt %).

Since the polymer obtained by this reaction is an insoluble solid, so that it is difficult to precisely determine the detailed molecular weight and degree of polymerization. Hence, the compositional ratio of the polymer was represented by the feed ratio of the individual reactants, assuming that the individual reactants participate in the polymerization with equivalent levels of reactivity. Production of the threefold cross-linked phosphane 4 under the heading was determined, based on the absence of a peak (at 115 ppm or around) assignable to vinyl group of Compound 1, in the result of $^{13}$C CP/MAS NMR measurement of the product.

NMR Data of Threefold Cross-Linked Polystyrene-Phosphane 4:
$^{31}$P CP/MAS: δ −6.2.
$^{13}$C CP/MAS: δ 34 (—CH(CH$_3$)$_3$), 36 (—CH(CH$_3$)$_3$), 39-59 (—CHArCH$_2$—), 127 (Ar), 145 (Ar), 149 (Ar).

Measurement of Phosphorus Content based on Threefold Cross-Linked Polystyrene-Phosphane 4-Rhodium Complex [RhCl(cod)(4)]

[Chemical Formula 8]

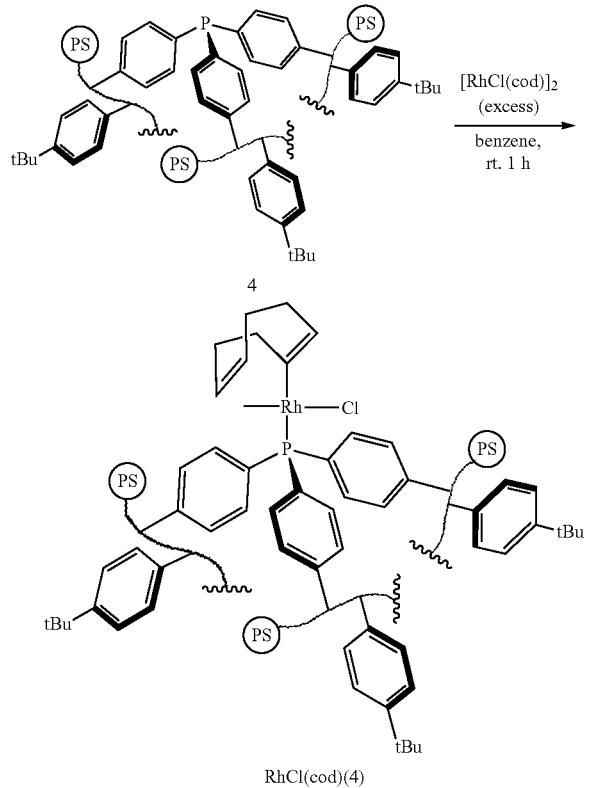

In a 10 mL Schlenk flask, a stirrer bar, threefold cross-linked polystyrene-phosphane 4 (200 mg), [RhCl(cod)]$_2$ (9.7 mg, 0.020 mmol) and benzene (2.0 mL) were placed, and the content was stirred at room temperature for one hour. Yellow beads were collected by filtration, washed with benzene, dried at 60° C. in vacuo, to obtain RhCl(cod)(4) (204 mg). The organic solvent in the filtrate was evaporated off under reduced pressure, to collect the unreacted portion of [RhCl(cod)]$_2$ (5.3 mg). Assuming that a phosphorus atom of 4 reacts with rhodium in a 1:1 ratio, the content of phosphorus atom was determined to be 0.09 mmol/g.

NMR Data of RhCl(cod)(4):
$^{31}$P CP/MAS: δ 28.1
$^{13}$C CP/MAS: δ 33 (—CH(CH$_3$)$_3$), 36 (—CH(CH$_3$)$_3$), 37-58 (—CHArCH$_2$—), 127 (Ar), 145 (Ar), 149 (Ar).

Although no signal assignable to cyclooctadiene was observed in the $^{13}$C CP/MAS measurement, production of the compound RhCl(cod)(4) under the heading was determined since a signal (28.1 ppm) in the $^{31}$P CP/MAS measurement was found to almost coincide with a $^{31}$P NMR (CDCl$_3$) signal (31.3 ppm, Tiburcio, *Polyhedron* 2006, 25, 1549.) of [RhCl(cod)(PPh$_3$)] which is a known compound with a similar structure.

Synthesis of Threefold Cross-Linked Polystyrene-Phosphane 5

[Chemical Formula 9]

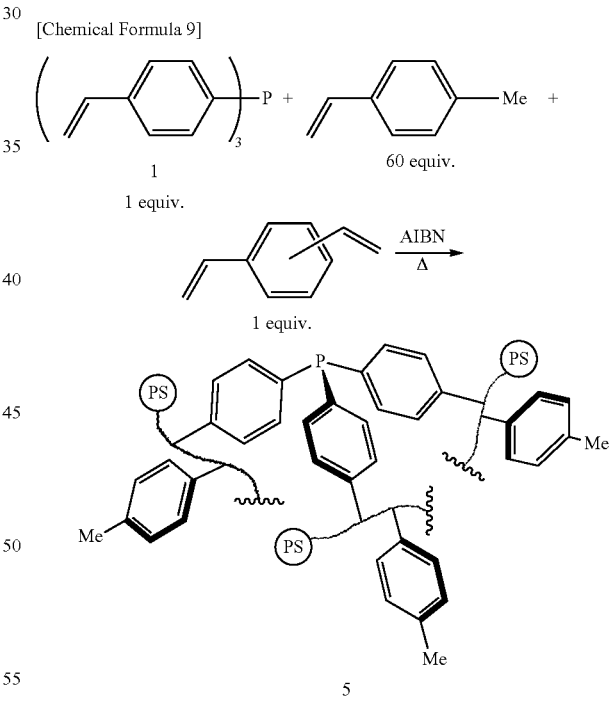

A stirrer bar was placed in a 500 mL three-necked, eggplant-shaped flask, then under an argon atmosphere, Compound 1 (0.17 g, 0.50 mmol), p-methyl styrene (3.6 g, 30 mmol), divinylbenzene (0.13 g, purity >50% (containing ethylvinylbenzene), >0.50 mmol), water (120 mL) and chlorobenzene (6.0 mL) were sequentially added. To the mixture, sodium chloride (3.0 g), Arabic gum (4.8 g) and azobisisobutyronitrile (0.050 g, 0.3 mmol) were added, the content was stirred under heating at 80° C. for 24 hours, so as to allow suspension polymerization to proceed. The reaction mixture was cooled down to room temperature, the insoluble matter was collected by filtration, sequentially washed with water, methanol, toluene, THF, and methanol, and dried at 80° C. in vacuo, to thereby obtain threefold cross-linked polystyrene-phosphane 5 in the form of white beady solid (2.4 g, 62 wt %).

Since the polymer obtained by this reaction is an insoluble solid, so that it is difficult to precisely determine the detailed molecular weight and degree of polymerization. Hence, the compositional ratio of the polymer was represented by the feed ratio of the individual reactants, assuming that the individual reactants participate in the polymerization with equivalent levels of reactivity. Production of the threefold cross-linked phosphane 5 under the heading was determined, based on the absence of a peak (at 115 ppm or around) assignable to vinyl group of Compound 1, in the result of $^{13}$C CP/MAS NMR measurement of the product. The content of phosphorus atom in 5 was determined to be 0.11 mmol/g, based on the complexation experiment with [RhCl(cod)]$_2$.

NMR Data of Threefold Cross-Linked Polystyrene-Phosphane 5:

$^{31}$P CP/MAS: δ −6.5.
$^{13}$C CP/MAS: δ 23 (CH$_3$C$_6$H$_4$—), 34-57 (—CHArCH$_2$—), 130 (Ar), 145 (Ar).

Synthesis of Threefold Cross-Linked Polystyrene-Phosphane 6 content was stirred under heating at 80° C. for 24 hours, so as to allow suspension polymerization to proceed. The reaction mixture was cooled down to room temperature, the insoluble matter was collected by filtration, washed sequentially with water, methanol, toluene, THF, and methanol, and dried at 80° C. in vacuo, to thereby obtain threefold cross-linked polystyrene-phosphane 6 in the form of white beady solid (3.0 g, 70 wt %).

Since the polymer obtained by this reaction is an insoluble solid, so that it is difficult to precisely determine the detailed molecular weight and degree of polymerization. Hence, the compositional ratio of the polymer was represented by the feed ratio of the individual reactants, assuming that the individual reactants participate in the polymerization with equivalent levels of reactivity. Production of the threefold cross-linked phosphane 6 under the heading was determined, based on the absence of a peak (at 115 ppm or around) assignable to vinyl group of Compound 1, in the result of $^{13}$C CP/MAS NMR measurement of the product. The content of phosphorus atom in 6 was determined to be 0.08 mmol/g, based on the complexation experiment with [RhCl(cod)]$_2$.

NMR Data of Threefold Cross-Linked Polystyrene-Phosphane 6:

$^{31}$P CP/MAS: δ−6.5.
$^{13}$C CP/MAS: δ 34-54 (—CHArCH$_2$—), 56 (CH$_3$OC$_6$H$_4$—), 115 (Ar), 129 (Ar), 160 (Ar).

Synthesis of Threefold Cross-Linked Polystyrene-Phosphane 7

[Chemical Formula 10]

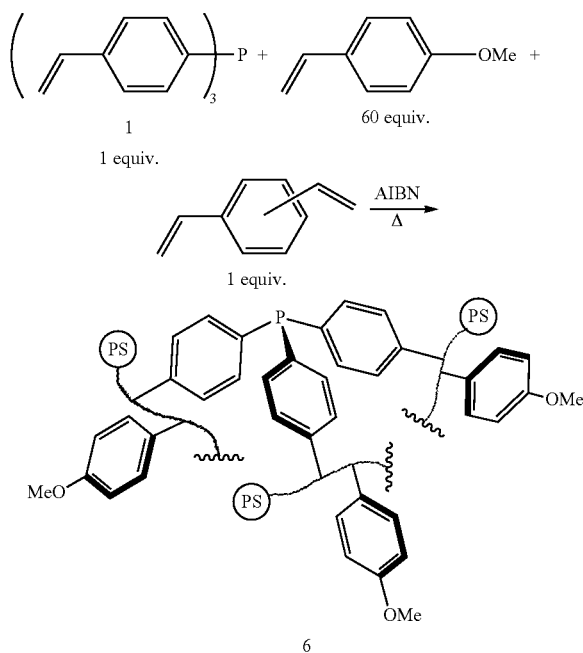

[Chemical Formula 11]

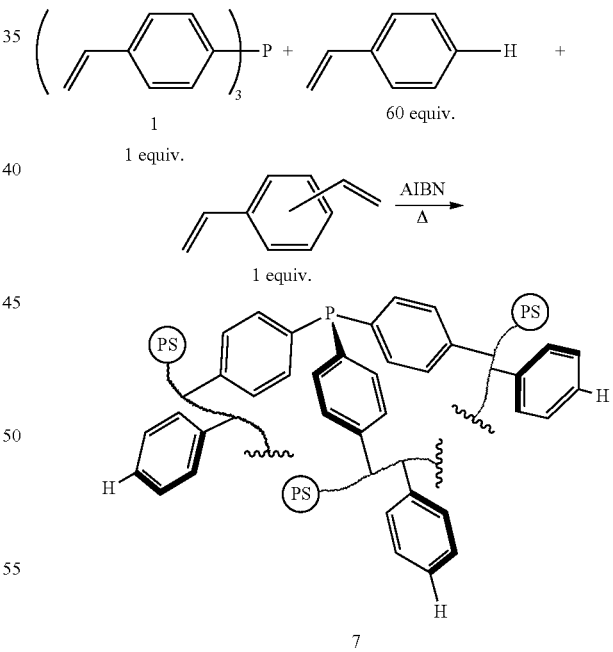

A stirrer bar was placed in a 500 mL three-necked, eggplant-shaped flask, then under an argon atmosphere, Compound 1 (0.17 g, 0.50 mmol), p-methoxy styrene (4.0 g, 30 mmol), divinylbenzene (0.13 g, purity >50% (containing ethylvinylbenzene), >0.50 mmol), water (120 mL) and chlorobenzene (6.0 mL) were sequentially added. To the mixture, sodium chloride (3.0 g), Arabic gum (4.8 g) and azobisisobutyronitrile (0.050 g, 0.3 mmol) were added, the A stirrer bar was placed in a 500 mL three-necked eggplant-shaped flask, then under an argon atmosphere, Compound 1 (0.17 g, 0.50 mmol), styrene (3.1 g, 30 mmol), divinylbenzene (0.13 g, purity >50% (containing ethylvinylbenzene), >0.50 mmol), water (120 mL) and chlorobenzene (6.0 mL) were sequentially added. To the mixture, sodium chloride (3.0 g), Arabic gum (4.8 g) and azobisisobutyronitrile (0.050 g, 0.3 mmol) were added, the content was stirred under heating at 80° C. for 24 hours, so as to allow suspension polymerization to proceed. The reaction mixture was cooled down to room temperature, the insoluble matter was collected by filtration, washed sequentially with water, methanol, toluene, THF, and methanol, and dried at 80° C. in vacuo, to thereby obtain threefold cross-linked polystyrene-phosphane 7 in the form of white beady solid (2.7 g, 81 wt %).

Since the polymer obtained by this reaction is an insoluble solid, so that it is difficult to precisely determine the detailed molecular weight and degree of polymerization. Hence, the compositional ratio of the polymer was represented by the feed ratio of the individual reactants, assuming that the individual reactants participate in the polymerization with equivalent levels of reactivity. Production of the threefold cross-linked phosphane 7 under the heading was determined, based on the absence of a peak (at 115 ppm or around) assignable to vinyl group of Compound 1, in the result of $^{13}$C CP/MAS NMR measurement of the product. The content of phosphorus atom in 7 was determined to be 0.12 mmol/g, based on the complexation experiment with [RhCl(cod)]$_2$.

NMR Data of Threefold Cross-Linked Polystyrene-Phosphane 7:
$^{31}$P CP/MAS: δ−7.3.
$^{13}$C CP/MAS: δ 34-58 (—CHArCH$_2$—), 130 (Ar), 148 (Ar).

Synthesis of Threefold Cross-Linked Polystyrene-Phosphane 8

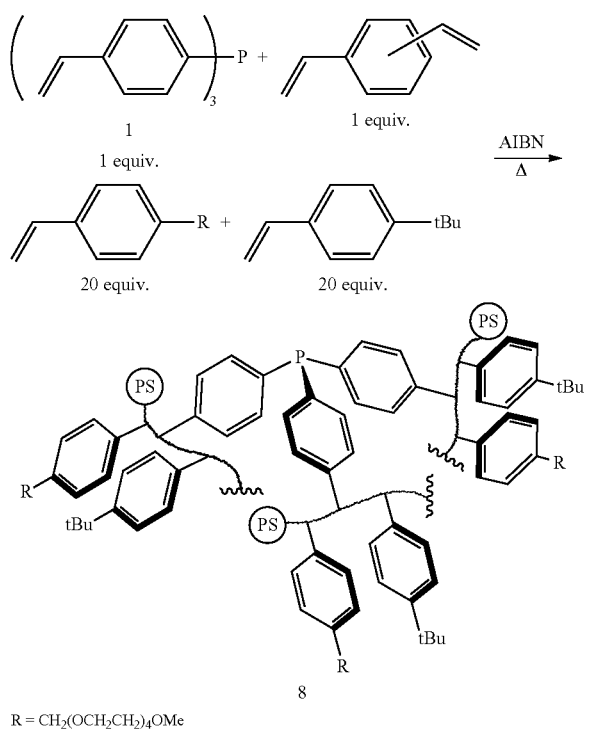

R = CH$_2$(OCH$_2$CH$_2$)$_4$OMe

A stirrer bar was placed in a 500 mL three-necked, eggplant-shaped flask, then under an argon atmosphere, Compound 1 (0.085 g, 0.25 mmol), p-(t-butyl)styrene (0.80 g, 5.0 mmol), p-vinylbenzyl{methyltetra(ethylene glycol)} (1.6 g, 5.0 mmol), divinylbenzene (0.065 g, purity >50% (containing ethylvinylbenzene), >0.25 mmol), water (60 mL) and chlorobenzene (3.0 mL) were sequentially added. To the mixture, sodium chloride (1.5 g), Arabic gum (2.4 g) and azobisisobutyronitrile (0.050 g, 0.3 mmol) were added, the content was stirred under heating at 80° C. for 24 hours, so as to allow suspension polymerization to proceed. The reaction mixture was cooled down to room temperature, the insoluble matter was collected by filtration, washed sequentially with water, methanol, toluene, THF, and methanol, and dried at 80° C. in vacuo, to thereby obtain threefold cross-linked polystyrene-phosphane 8 in the form of white beady solid (2.1 g, 81 wt %).

Since the polymer obtained by this reaction is an insoluble solid, so that it is difficult to precisely determine the detailed molecular weight and degree of polymerization. Hence, the compositional ratio of the polymer was represented by the feed ratio of the individual reactants, assuming that the individual reactants participate in the polymerization with equivalent levels of reactivity. Production of the threefold cross-linked phosphane 8 under the heading was determined, based on the absence of a peak (at 115 ppm or around) assignable to vinyl group of Compound 1, in the result of $^{13}$C CP/MAS NMR measurement of the product. The content of phosphorus atom in 8 was determined to be 0.10 mmol/g, based on the complexation experiment with [RhCl(cod)]$_2$.

NMR Data of Threefold Cross-Linked Polystyrene-Phosphane 8:
$^{31}$P CP/MAS: δ−6.4.
$^{13}$C CP/MAS: δ 34 (—C(CH$_3$)$_3$), 36 (—C(CH$_3$)$_3$), 38-58 (—CHArCH$_2$—), 61 (—OCH$_3$), 73 (—CH$_2$O—, —OCH$_2$CH$_2$O—), 129 (Ar), 138 (Ar), 145 (Ar), 150 (Ar).

Synthesis of Twofold Cross-Linked Polystyrene-Phosphane 9

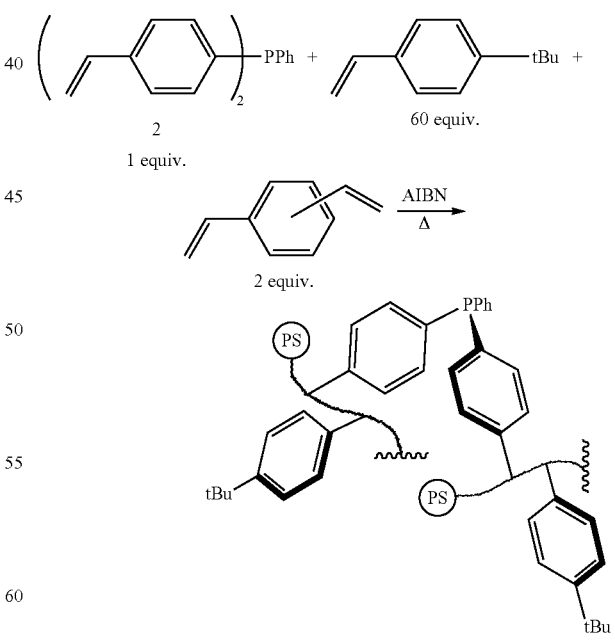

A stirrer bar was placed in a 500 mL three-necked, eggplant-shaped flask, then under an argon atmosphere, Compound 2 (0.14 g, 0.50 mmol), p-(t-butyl)styrene (4.8 g, 30 mmol), divinylbenzene (0.26 g, purity >50% (containing ethylvinylbenzene), >1.0 mmol), water (120 mL) and chlorobenzene (6.0 mL) were sequentially added. To the mixture, sodium chloride (3.0 g), Arabic gum (4.8 g) and azobisisobutyronitrile (0.050 g, 0.30 mmol) were added, the content was stirred under heating at 80° C. for 24 hours, so as to allow suspension polymerization to proceed. The reaction mixture was cooled down to room temperature, the insoluble matter was collected by filtration, washed sequentially with water, methanol, toluene, THF, and methanol, and dried at 80° C. in vacuo, to thereby obtain twofold cross-linked polystyrene-phosphane 9 in the form of white beady solid (3.0 g, 57 wt %).

Since the polymer obtained by this reaction is an insoluble solid, so that it is difficult to precisely determine the detailed molecular weight and degree of polymerization. Hence, the compositional ratio of the polymer was represented by the feed ratio of the individual reactants, assuming that the individual reactants participate in the polymerization with equivalent levels of reactivity. Production of the twofold cross-linked phosphane 9 under the heading was determined, based on the absence of a peak (at 115 ppm or around) assignable to vinyl group of Compound 2, in the result of $^{13}$C CP/MAS NMR measurement of the product. The content of phosphorus atom in 9 was determined to be 0.12 mmol/g, based on the complexation experiment with [RhCl(cod)]$_2$.

NMR Data of Twofold Cross-Linked Polystyrene-Phosphane 9:
$^{31}$P CP/MAS: δ-5.7.
$^{13}$C CP/MAS: δ 33 (—CH(CH$_3$)$_3$), 36 (—CH(CH$_3$)$_3$), 38-58 (—CHArCH$_2$—), 127 (Ar), 145 (Ar), 150 (Ar).

Synthesis of Singlefold Cross-Linked Polystyrene-Phosphane 10

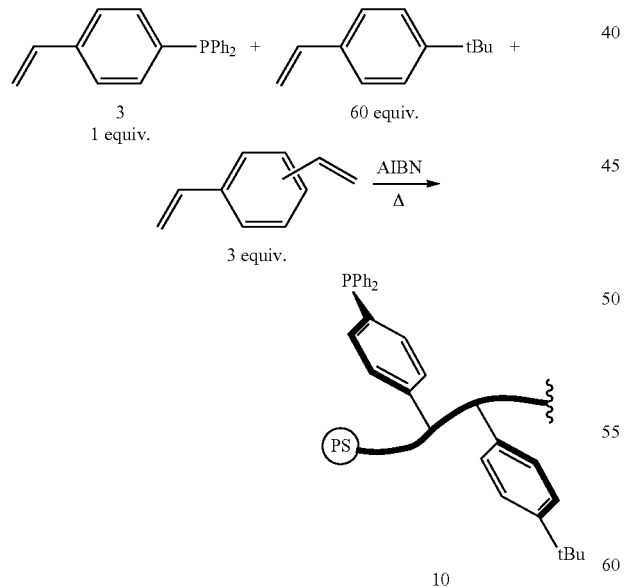

[Chemical Formula 14]

A stirrer bar was placed in a 500 mL three-necked eggplant-shaped flask, then under an argon atmosphere, Compound 3 (0.17 g, 0.50 mmol), p-(t-butyl)styrene (4.8 g, 30 mmol), divinylbenzene (0.39 g, purity >50% (containing ethylvinylbenzene), >1.50 mmol), water (120 mL) and chlorobenzene (6.0 mL) were sequentially added. To the mixture, sodium chloride (3.0 g), Arabic gum (4.8 g) and azobisisobutyronitrile (0.050 g, 0.30 mmol) were added, the content was stirred under heating at 80° C. for 24 hours, so as to allow suspension polymerization to proceed. The reaction mixture was cooled down to room temperature, the insoluble matter was collected by filtration, washed sequentially with water, methanol, toluene, THF, and methanol, and dried at 80° C. in vacuo, to thereby obtain singlefold cross-linked polystyrene-phosphane 10 in the form of white beady solid (3.4 g, 64 wt %).

Since the polymer obtained by this reaction is an insoluble solid, so that it is difficult to precisely determine the detailed molecular weight and degree of polymerization. Hence, the compositional ratio of the polymer was represented by the feed ratio of the individual reactants, assuming that the individual reactants participate in the polymerization with equivalent levels of reactivity. Production of the singlefold cross-linked phosphane 10 under the heading was determined, based on the absence of a peak (at 115 ppm or around) assignable to vinyl group of Compound 3, in the result of $^{13}$C CP/MAS NMR measurement of the product. The content of phosphorus atom in 10 was determined to be 0.09 mmol/g, based on the complexation experiment with [RhCl(cod)]$_2$.

NMR Data of Singlefold Cross-Linked Polystyrene-Phosphane 10:
$^{31}$P CP/MAS: δ-5.7.
$^{13}$C CP/MAS: δ 33 (—CH(CH$_3$)$_3$), 36 (—CH(CH$_3$)$_3$), 37-57 (—CHArCH$_2$—), 127 (Ar), 145 (Ar), 150 (Ar).

Experimental Complexation Between PdCl$_2$(PhCN)$_2$ and 4

[Chemical Formula 15]

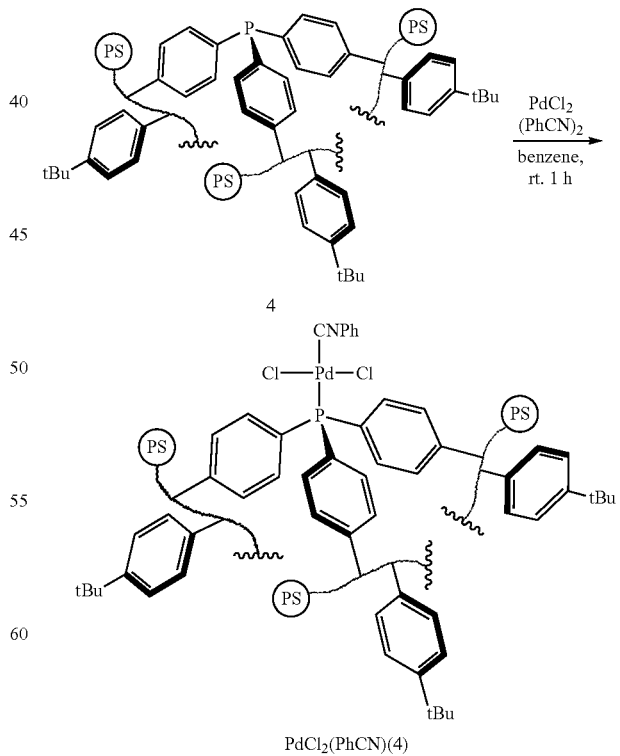

In a 10 mL Schlenk flask, a stirrer bar, threefold cross-linked polystyrene-phosphane 4 (0.20 g, P: 0.018 mmol) and PdCl$_2$(PhCN)$_2$ (3.5 mg, 0.0090 mmol) were placed, then under an argon atmosphere, 2 mL of benzene was added, and the content was stirred at room temperature for one hour. The reaction product was collected by filtration, washed with benzene, dried at 60° C. in vacuo, to thereby obtain a transition metal complex (0.20 g) having the threefold cross-linked polystyrene-phosphane 4 as a ligand. Unreacted 4 and production of PdCl$_2$(PhCN)(4) were determined by $^{31}$P CP/MAS NMR measurement of the polymer after the reaction.

NMR Data of Polymer after Reaction:
$^{31}$P CP/MAS: δ–6.9 (PAr$_3$), 33.2 (Pd—PAr$_3$).

Experimental Complexation between PdCl$_2$(PhCN)$_2$ and 10

[Chemical Formula 16]

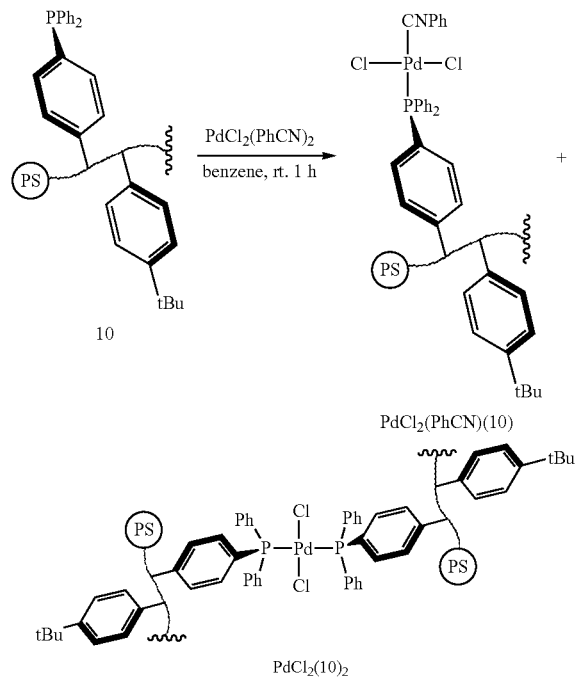

In a 10 mL Schlenk flask, a stirrer bar, threefold cross-linked polystyrene-phosphane 10 (0.20 g, P: 0.018 mmol) and PdCl$_2$(PhCN)$_2$ (3.5 mg, 0.009 mmol) were placed, then under an argon atmosphere, 2 mL of benzene was added, and the content was stirred at room temperature for one hour. The reaction product was collected by filtration, washed with benzene, dried at 60° C. in vacuo, to thereby obtain a transition metal complex (0.20 g) having threefold cross-linked polystyrene-phosphane 10 as a ligand. Unreacted 10 and production of PdCl$_2$(PhCN)(10) and PdCl$_2$(10)$_2$ were determined by $^{31}$P CP/MAS NMR measurement of the polymer after the reaction.

NHR Data of Polymer after Reaction:
$^{31}$P CP/MAS: δ–5.5 (PAr$_3$), 23.8 (Pd—(PAr$_3$)$_2$), 31.1 (Pd—PAr$_3$).

Suzuki-Miyaura Cross Coupling Reaction Using Aryl Chloride as Substrate

Under a nitrogen atmosphere, a stirrer bar and a ligand (P: 0.010 mmol) were placed in a 10 mL Schlenk flask. A tetrahydrofuran solution (1 mL) of PdCl$_2$(PhCN)$_2$ (1.9 mg, 0.0050 mmol) was added, and the content was stirred at room temperature for 5 minutes. Then, K$_3$PO$_4$ (318 mg, 1.5 mmol), phenylboronic acid (91.4 mg, 0.75 mmol) and 4-chlorotoluene (63.3 mg, 0.50 mmol) were sequentially added. The content was then stirred and allowed to react under heating at 40° C. for two hours. The percent yield of 4-methylbiphenyl, which is a target coupling product, was calculated based on $^1$H NMR measurement using 1,1,2,2-tetrachloroethane (0.50 mmol) as an internal standard. Results of ligand effect are shown in Table 1. The crude product was further purified by silica gel column chromatography (hexane), to isolate the coupling product. Example 1: yield=71 mg, percent yield=85%

NMR Data of 4-Methylbiphenyl:
$^1$H NMR (CDCl$_3$): δ 2.40 (s, 3H), 7.22-7.28 (m, 2H), 7.28-7.37 (m, 1H), 7.38-7.47 (m, 2H), 7.48-7.54 (m, 2H), 7.55-7.62 (m, 2H).
$^{13}$C NMR (CDCl$_3$): δ 20.95, 127.03 (3C), 127.05 (2C), 128.77 (2C), 129.54 (2C), 137.08, 138.44, 141.25.

TABLE 1

Ligand Effect in Suzuki-Miyaura Cross Coupling Reaction

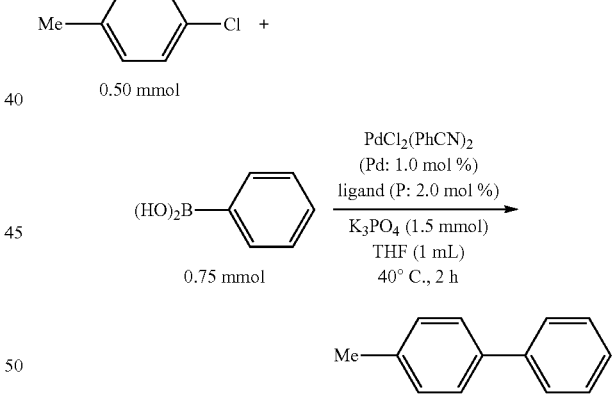

| Example | Ligand | NMR Percent Yield (%) |
|---|---|---|
| 1 (Example) | Threefold cross-linked polystyrene-phosphane 4 | 95 (85) |
| 2 (Example) | Threefold cross-linked polystyrene-phosphane 5 | 82 |
| 3 (Example) | Threefold cross-linked polystyrene-phosphane 6 | 84 |
| 4 (Example) | Threefold cross-linked polystyrene-phosphane 7 | 71 |
| 5 (Example) | Threefold cross-linked polystyrene-phosphane 8 | 82 |
| 6 (Comparative Example) | Twofold cross-linked polystyrene-phosphane 9 | 52 |
| 7 (Comparative Example) | Singlefold cross-linked polystyrene-phosphane 10 | 6 |
| 8 (Reference Example) | Compound 1 | 0 |

TABLE 1-continued

Ligand Effect in Suzuki-Miyaura Cross Coupling Reaction

| | | |
|---|---|---|
| 9 (Reference Example) | PPh₃ | 0 |
| 10 (Reference Example) | none | 0 |

Reaction conditions:
4-chlorotoluene (0.50 mmol), phenylboronic acid (0.75 mmol), PdCl₂(PhCN)₂ (0.0050 mmol, 1.0 mol %), ligand (P: 0.010 mmol, 2.0 mol %), K₃PO₄ (1.5 mmol), THF (1.0 mL), 40° C., 2 hours.
Numeral in the parentheses represents isolated yield.

Aqueous Suzuki-Miyaura Coupling Reaction with Palladium Catalyst Using Aryl Chloride as Substrate Under a nitrogen atmosphere, a stirrer bar, a ligand (P: 0.010 mmol), PdCl₂(PhCN)₂ (1.9 mg, 0.005 mmol) and tetrahydrofuran (1 mL) were placed in a 10 mL Schlenk flask, and the content was stirred at room temperature for 5 minutes. The solvent was evaporated off under reduced pressure, then again in a nitrogen atmosphere, K₃PO₄ (318 mg, 1.5 mmol), phenylboronic acid (91.4 mg, 0.75 mmol), 4-chlorotoluene (63.3 mg, 0.5 mmol), and H₂O (1 mL) were sequentially added. Then, the content was stirred and allowed to react under heating at 40° C. for two hours. The percent yield of 4-methylbiphenyl, which is a target coupling product, was calculated based on ¹H NMR measurement using 1,1,2,2-tetrachloroethane (0.50 mmol) as an internal standard. Results of ligand effect are shown in Table 2. The crude product was further purified by silica gel column chromatography (hexane), to isolate the coupling product. Example 13: yield=60 mg, percent yield=71%

TABLE 2

Ligand Effect in Aqueous Suzuki-Miyaura Cross Coupling Reaction

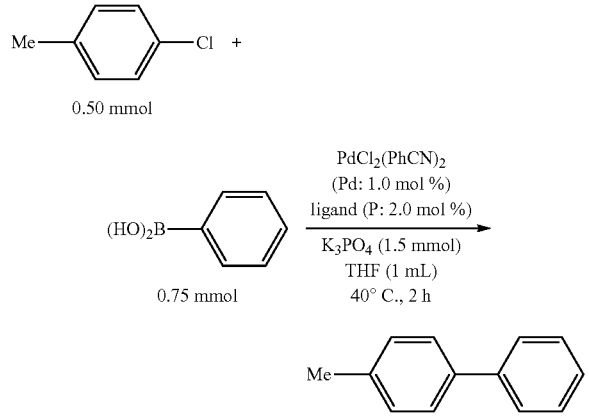

| Example | Ligand | NMR Percent Yield (%) |
|---|---|---|
| 11 (Example) | Threefold cross-linked polystyrene-phosphane 4 | 0 |
| 12 (Example) | Threefold cross-linked polystyrene-phosphane 5 | 18 |
| 13 (Example) | Threefold cross-linked polystyrene-phosphane 6 | 79 (71) |
| 14 (Example) | Threefold cross-linked polystyrene-phosphane 7 | 18 |
| 15 (Example) | Threefold cross-linked polystyrene-phosphane 8 | 49 |
| 16 (Comparative Example) | Twofold cross-linked polystyrene-phosphane 9 | 0 |
| 17 (Comparative Example) | Singlefold cross-linked polystyrene-phosphane 10 | 0 |
| 18 (Reference Example) | Compound 1 | 0 |

TABLE 2-continued

Ligand Effect in Aqueous Suzuki-Miyaura Cross Coupling Reaction

| | | |
|---|---|---|
| 19 (Reference Example) | PPh₃ | 0 |
| 20 (Reference Example) | None | 0 |

Reaction conditions:
4-chlorotoluene (0.50 mmol), phenylboronic acid (0.75 mmol), PdCl₂(PhCN)₂ (0.0050 mmol, 1.0 mol %), ligand (P: 0.010 mmol, 2.0 mol %), K₃PO₄ (1.5 mmol), H₂O (1.0 mL), 40° C., 2 hours.
Numeral in the parentheses represents isolated yield.

Buchwald-Hartwig Amination with Palladium Catalyst Using Aryl Chloride as Substrate Under a nitrogen atmosphere, a stirrer bar and a ligand (P: 0.0050 mmol) were placed in a 10 mL Schlenk flask. A toluene solution (0.8 mL) of [PdCl(allyl)]₂ (0.46 mg, 0.013 mmol) was added, and the content was stirred at room temperature for 5 minutes. Then, t-butanol (0.2 mL), KOtBu (46 mg, 0.35 mmol), 4-butyl chlorobenzene (42 mg, 0.25 mmol) and aniline (28 mg, 0.30 mmol) were sequentially added. The content was then stirred and allowed to react under heating at 100° C. for 20 hours. The percent yield of 4-butyl-N-phenylaniline, which is a target coupling product, was calculated based on ¹H NMR measurement using 1,1,2,2-tetrachloroethane (0.25 mmol) as an internal standard. Results of ligand effect are shown in Table 3. The crude product was further purified by silica gel column chromatography (hexane:ethyl acetate=90:10), to isolate the coupling product. Example 21: yield=45 mg, percent yield=80%

NMR Data of 4-Butyl-N-Phenylaniline:
¹H NMR (CDCl₃): δ 0.93 (t, J=7.5 Hz, 3H), 1.29-1.43 (m, 2H), 1.52-1.64 (m, 2H), 2.56 (t, J=7.5 Hz, 2H), 5.61 (s, 1H), 6.84-6.91 (m, 1H), 7.00-7.05 (m, 4H), 7.07-7.11 (m, 2H), 7.20-7.28 (m, 2H).
¹³C NMR (CDCl₃): δ 18.86, 22.23, 33.73, 34.83, 116.97 (2C), 118.72 (2C), 120.34, 129.23 (2C), 129.36 (2C), 136.12, 140.54, 143.95.

TABLE 3

Ligand Effect in Buchwald-Hartwig Amination

| Example | Ligand | NMR Percent Yield % |
|---|---|---|
| 21 (Example) | Threefold cross-linked polystyrene-phosphane 4 | 99 (80) |

TABLE 3-continued

Ligand Effect in Buchwald-Hartwig Amination

| | | |
|---|---|---|
| 22 (Example) | Threefold cross-linked polystyrene-phosphane 5 | 92 |
| 23 (Example) | Threefold cross-linked polystyrene-phosphane 6 | 51 |
| 24 (Example) | Threefold cross-linked polystyrene-phosphane 7 | 51 |
| 25 (Example) | Threefold cross-linked polystyrene-phosphane 8 | 40 |
| 26 (Comparative Example) | Twofold cross-linked polystyrene-phosphane 9 | 22 |
| 27 (Comparative Example) | Singlefold cross-linked polystyrene-phosphane 10 | 5 |
| 28 (Reference Example) | Compound 1 | <1 |
| 29 (Reference Example) | PPh$_3$ | <1 |
| 30 (Reference Example) | None | <1 |

Reaction Conditions:
aryl chloride (0.25 mmol), aniline (0.30 mmol), [PdCl(allyl)]$_2$ (0.00125 mmol, Pd: 0.0025 mmol, 1.0 mol %), ligand (P: 0.0050 mmol, 2.0 mol %), KOtBu (0.35 mmol), toluene/tBuOH (1.0 mL, 4:1), 100° C., 20 hours.
Numeral in the parentheses represents isolated yield.

C(sp$^3$)-H Borylation with Iridium Catalyst

Under a nitrogen atmosphere, a stirrer bar, a ligand (P: 0.0060 mmol) and bis(pinacolato)diboron (76 mg, 0.30 mmol) were placed in a 10 mL Schlenk flask. To the content, a cyclopentyl methyl ether solution (1.0 mL) of [Ir(OMe)(cod)]$_2$ (2.0 mg, 0.0030 mmol), and 2-pentylpyridine (135 mg, 0.90 mmol) were added, the content was stirred and allowed to react under heating at 60° C. for 15 hours. The percent yield of 2-(2-pinacolatoborylpentyl)pyridine, which is a target coupling product, was calculated based on $^1$H NMR measurement using 1,1,2,2-tetrachloroethane (0.30 mmol) as an internal standard. Results of ligand effect are shown in Table 4. The crude product was further purified by vacuum distillation, to isolate the target borylation product.
Example 31: yield=35 mg, percent yield=42%
NMR Data of 2-(2-Pinacolatoborylpentyl)pyridine:

$^1$H NMR (CDCl$_3$): δ 0.88 (t, J=7.1 Hz, 3H), 1.10-1.18 (m, 2H), 1.23 (s, 6H), 1.24 (s, 6H), 1.29-1.40 (m, 2H), 1.42-1.55 (m, 1H), 2.82 (dd, J=16.2, 6.6 Hz, 1H), 3.07 (dd, J=16.2, 6.6 Hz, 1H), 7.22 (t, J=5.7 Hz, 1H), 7.28 (d, J=7.4 Hz, 1H), 7.71 (td, J=7.4, 0.9 Hz, 1H), 8.55 (d, J=7.1 Hz, 1H).

$^{13}$C NMR (CDCl$_3$): δ 14.25, 22.22, 25.49 (2C), 25.58 (2C), 33.27, 38.08, 80.83, 80.85, 121.64, 123.46, 138.42, 144.80, 162.70. Signal assignable to carbon directly bound to boron was not observed.

TABLE 4

Ligand Effect in C(sp$^3$)-H Borylation

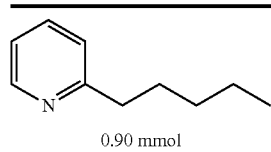

TABLE 4-continued

Ligand Effect in C(sp$^3$)-H Borylation

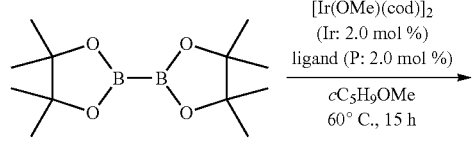

| Experimental No. | Ligand | NMR Percent Yield (%) |
|---|---|---|
| 31 (Example) | Threefold cross-linked polystyrene-phosphane 4 | 82 (42) |
| 32 (Example) | Threefold cross-linked polystyrene-phosphane 5 | 81 |
| 33 (Example) | Threefold cross-linked polystyrene-phosphane 6 | 61 |
| 34 (Example) | Threefold cross-linked polystyrene-phosphane 7 | 21 |
| 35 (Example) | Threefold cross-linked polystyrene-phosphane 8 | 3 |
| 36 (Comparative Example) | Twofold cross-linked polystyrene-phosphane 9 | 61 |
| 37 (Comparative Example) | Singlefold cross-linked polystyrene-phosphane 10 | 45 |
| 38 (Reference Example) | Compound 1 | 15 |
| 39 (Reference Example) | PPh$_3$ | 0 |
| 40 (Reference Example) | None | 0 |

Reaction Conditions:
2-pentylpyridine (0.90 mmol), bis(pinacolato)diboron (0.30 mmol), [Ir(OMe)(cod)]$_2$ (0.0030 mmol, Ir: 0.0060 mmol, 1.0 mol %), ligand (P: 0.0060 mmol, 2.0 mol %), cyclopentyl methyl ether (1.0 mL), 60° C., 15 hours.
Numeral in the parentheses represents isolated yield.

Evaluation of Swelling Characteristics of Cross-Linked Polystyrene-Phosphane:

In a 1.0 mL graduated syringe having a piece of filter paper laid therein, 100 mg of cross-linked polystyrene-phosphane (dry volume: 1.8 mL/g) was placed, then 1.0 mL of an appropriate organic solvent was added, and the content was allowed to stand still for 30 minutes. The excessive solvent was removed, and the volume of swelled polymer was measured. Results are summarized in Table 5 and Table 6.

TABLE 5 swelling volume of Cross-Liked Polystyrene-Phosphane

| Experimental No. | Cross-Liked Polystyrene-Phosphane | Swelling Volume in Toluene (mL/g) | Swelling Volume in Cyclopentyl Methyl Ether (mL/g) |
|---|---|---|---|
| 41 (Example) | Threefold cross-linked polystyrene-phosphane 4 | 5.8 | 5.9 |
| 42 (Example) | Threefold cross-linked polystyrene-phosphane 5 | 5.8 | 5.6 |
| 43 (Example) | Threefold cross-linked polystyrene-phosphane 6 | 5.0 | 3.7 |
| 44 (Example) | Threefold cross-linked polystyrene-phosphane 7 | 5.0 | 4.6 |
| 45 (Example) | Threefold cross-linked polystyrene-phosphane 8 | 5.6 | 3.1 |
| 46 (Example) | Twofold cross-linked polystyrene-phosphane 9 | 5.2 | 6.4 |
| 47 (Example) | Singlefold cross-linked polystyrene-phosphane 10 | 5.6 | 5.4 |

TABLE 6

Swelling Volume of Threefold Cross-Linked Polystyrene-Phosphane 4

| Experimental No. | Solvent | Swelling Volume (mL/g) |
|---|---|---|
| 48 (Example) | Tetrahydrofuran | 5.0 |
| 49 (Example) | t-Butyl methyl ether | 4.6 |
| 50 (Example) | Ethyle acetate | 4.0 |
| 51 (Example) | Diethyl ether | 3.8 |
| 52 (Example) | Acetone | 2.6 |
| 53 (Example) | Hexane | 2.4 |
| 54 (Example) | Dimethylformamide | 2.1 |
| 55 (Example) | Methanol | 2.0 |

INDUSTRIAL APPLICABILITY

This invention is useful in technical fields where transition metal complexes are involved.

What is claimed is:

1. A complex comprising a polymer compound and a transition metal, wherein the polymer compound comprises a threefold styrene cross-linked phosphane unit and styrene units each having a substituent R at the 4-position, wherein R represents a hydrogen atom, a lower alkyl group having 1 to 6 carbon atoms, a lower alkoxy group having 1 to 6 carbon atoms, or a polar functional group, wherein the styrene units have substituents R which are the same or different, and wherein the polymer compound binds to the transition metal only through a phosphine group in the threefold styrene cross-linked phosphane unit.

2. The complex according to claim 1, further comprising, as a ligand, an atom or group selected from halogen, carbonyl, hydroxy, nitro, amino, sulfonyl, and cyano.

3. The complex according to claim 2, wherein when the ligand is carbonyl, the carbonyl is present in a group selected from ester, aldehyde, ketone, and amide.

4. The complex according to claim 1, wherein the transition metal is selected from palladium, iridium, rhodium, platinum, ruthenium, nickel, and copper.

5. The complex according to claim 1, comprising a structure (1) below:

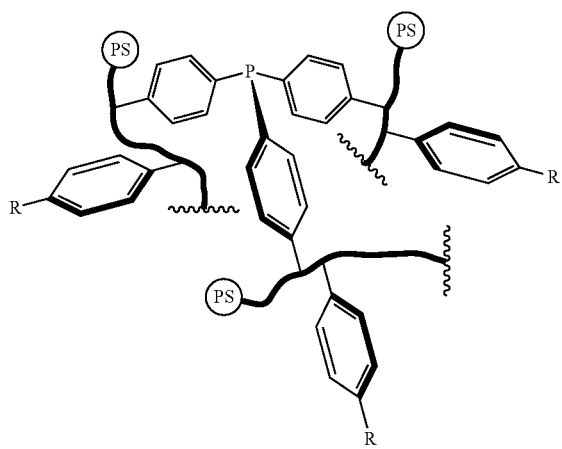

(1)

wherein PS represents a polystyrene unit chain composed of the styrene units each having the substituent R.

6. The complex according to claim 1, wherein the polymer compound is a copolymer of a tris(4-vinylphenyl)phosphane unit and the styrene units each having a substituent R, wherein the substituents R are the same or different, and when the substituents R are different, the styrene units having different substituents R are contained in the polymer compound with random arrangement.

7. The complex according to claim 6, wherein an equivalence ratio of the tris(4-vinylphenyl)phosphane unit and the styrene units each having a substituent R falls in a range of 1:(20 to 1000).

8. The complex according to claim 7, wherein the copolymer further contains crosslinkage through a divinylbenzene unit.

9. The complex according to claim 8, wherein the equivalence ratio of the tris(4-vinylphenyl)phosphane unit, the styrene units each having a substituent R and the divinylbenzene unit falls in a range of 1:(20 to 1000):(0.1 to 20).

10. The complex according to claim 1, wherein the polymer compound exhibits a swelling volume in toluene or cyclopentyl methyl ether of 2.0 to 7.0 mL/g.

11. The complex according to claim 1, wherein the polar functional group is selected from a hydroxy group, a polyether group, an acetoxy group, an ester group, and an amide group.

12. The complex according to claim 1, wherein the polymer compound contains no metal.

13. A method of preparation of a complex, the method comprising reacting a polymer compound and a transition metal comprising compound to obtain a complex, wherein the polymer compound comprises a threefold styrene cross-linked phosphane unit and styrene units each having a substituent R at the 4-position, wherein R represents a hydrogen atom, a lower alkyl group having 1 to 6 carbon atoms, a lower alkoxy group having 1 to 6 carbon atoms, or a polar functional group, wherein the styrene units have substituents R which are the same or different, and wherein the polymer compound binds to the transition metal only through a phosphine group in the threefold styrene cross-linked phosphane unit.

14. The method according to claim 13, comprising a structure (1) below:

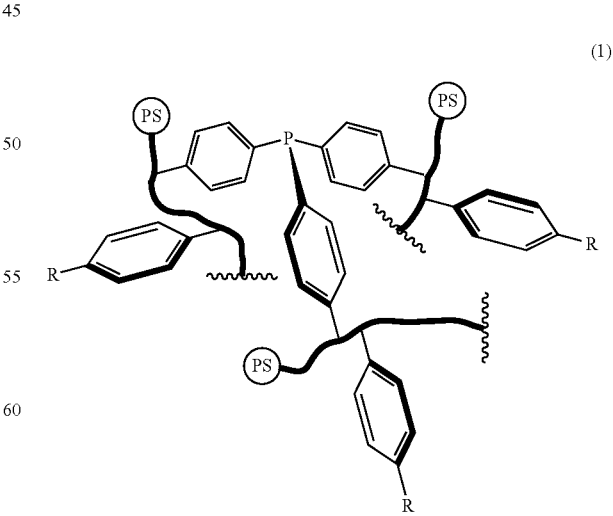

(1)

wherein PS represents a polystyrene unit chain composed of the styrene units each having the substituent R.

15. The method according to claim 13, wherein the polymer compound is a copolymer of a tris(4-vinylphenyl)phosphane unit and the styrene units each having a substituent R, wherein the substituents R are the same or different, and when the substituents R are different, the styrene units having different substituents R are contained in the polymer compound with random arrangement.

16. The method according to claim 15, wherein an equivalence ratio of the tris(4-vinylphenyl)phosphane unit and the styrene units each having a substituent R falls in a range of 1:(20 to 1000).

17. The method according to claim 15, wherein the copolymer further contains crosslinkage through a divinylbenzene unit.

18. The method according to claim 17, wherein the equivalence ratio of the tris(4-vinylphenyl)phosphane unit, the styrene units each having a substituent R and the divinylbenzene unit falls in a range of 1:(20 to 1000):(0.1 to 20).

19. The method according to claim 13, wherein the polymer compound exhibits a swelling volume in toluene or cyclopentyl methyl ether of 2.0 to 7.0 mL/g.

20. The method according to claim 13, wherein the polar functional group is selected from a hydroxy group, a polyether group, an acetoxy group, an ester group, and an amide group.

21. The method according to claim 13, wherein the polymer compound contains no metal.

22. A method of carrying out a coupling reaction of organic compounds, the method comprising performing the coupling reaction in the presence of a catalyst, wherein the catalyst comprises the complex according to claim 1.

23. The method according to claim 22, wherein the coupling reaction is selected from a C—C coupling reaction, a C—N coupling reaction, and a $C(sp^3)$-H borylation.

* * * * *

UNITED STATES PATENT AND TRADEMARK OFFICE
CERTIFICATE OF CORRECTION

PATENT NO. : 10,010,879 B2
APPLICATION NO. : 14/772424
DATED : July 3, 2018
INVENTOR(S) : Masaya Sawamura et al.

It is certified that error appears in the above-identified patent and that said Letters Patent is hereby corrected as shown below:

On the Title Page

Item [73] should read:
National University Corporation Hokkaido University, Sapporo-shi, Hokkaido (JP);
Tosoh Organic Chemical Co., Ltd, Shunan, Yamaguchi (JP)

Signed and Sealed this
Thirtieth Day of October, 2018

Andrei Iancu
*Director of the United States Patent and Trademark Office*